(12) United States Patent
Chu

(10) Patent No.: US 7,163,395 B2
(45) Date of Patent: *Jan. 16, 2007

(54) DENTAL MEASUREMENT INSTRUMENTS

(76) Inventor: Stephen J. Chu, 205 E. 64th St., Suite 502, New York, NY (US) 10021

( * ) Notice: Subject to any disclaimer, the term of this patent is extended or adjusted under 35 U.S.C. 154(b) by 0 days.

This patent is subject to a terminal disclaimer.

(21) Appl. No.: 10/896,466

(22) Filed: Jul. 22, 2004

(65) Prior Publication Data

US 2005/0266372 A1 Dec. 1, 2005

Related U.S. Application Data

(63) Continuation-in-part of application No. 10/854,667, filed on May 26, 2004, now Pat. No. 7,059,852.

(51) Int. Cl.
*A62C 19/14* (2006.01)

(52) U.S. Cl. .......................................................... 433/72

(58) Field of Classification Search .................. 433/72; 33/511, 513, 514
See application file for complete search history.

(56) References Cited

U.S. PATENT DOCUMENTS

| 5,176,516 A | * | 1/1993 | Koizumi | 433/72 |
| 6,726,472 B1 | * | 4/2004 | Kuhn | 33/514 |
| 6,783,359 B1 | * | 8/2004 | Kapit | 433/3 |

* cited by examiner

*Primary Examiner*—Cary E. O'Connor
(74) *Attorney, Agent, or Firm*—Howard C. Miskin, Esq.; Gloria Tsui-Yip, Esq.

(57) ABSTRACT

A dental measurement instrument having a handle and a measuring gauge extending from one end of the handle. In one embodiment, the measuring gauge has at least two calibrated measurement shafts, each shaft bearing a plurality of calibration indicia. The calibration indicia on the two shafts are correlated with each other in a specific predetermined mathematical relationship.

13 Claims, 18 Drawing Sheets

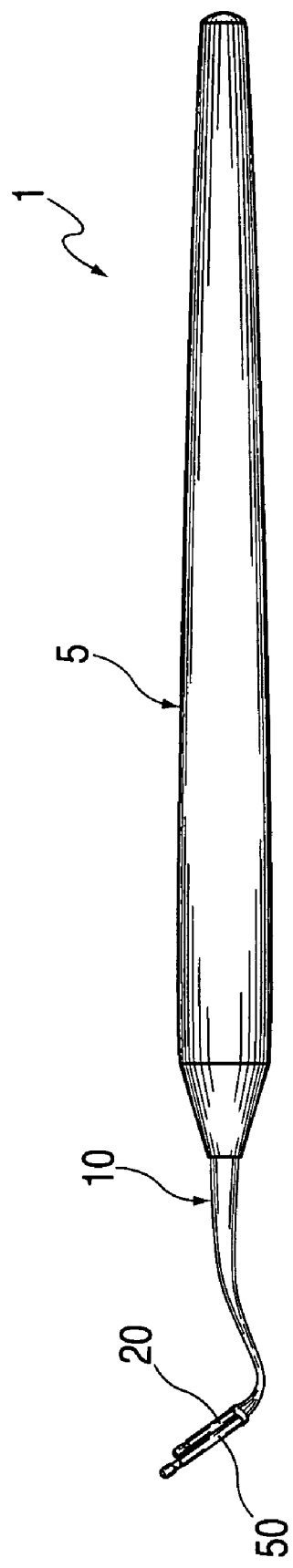
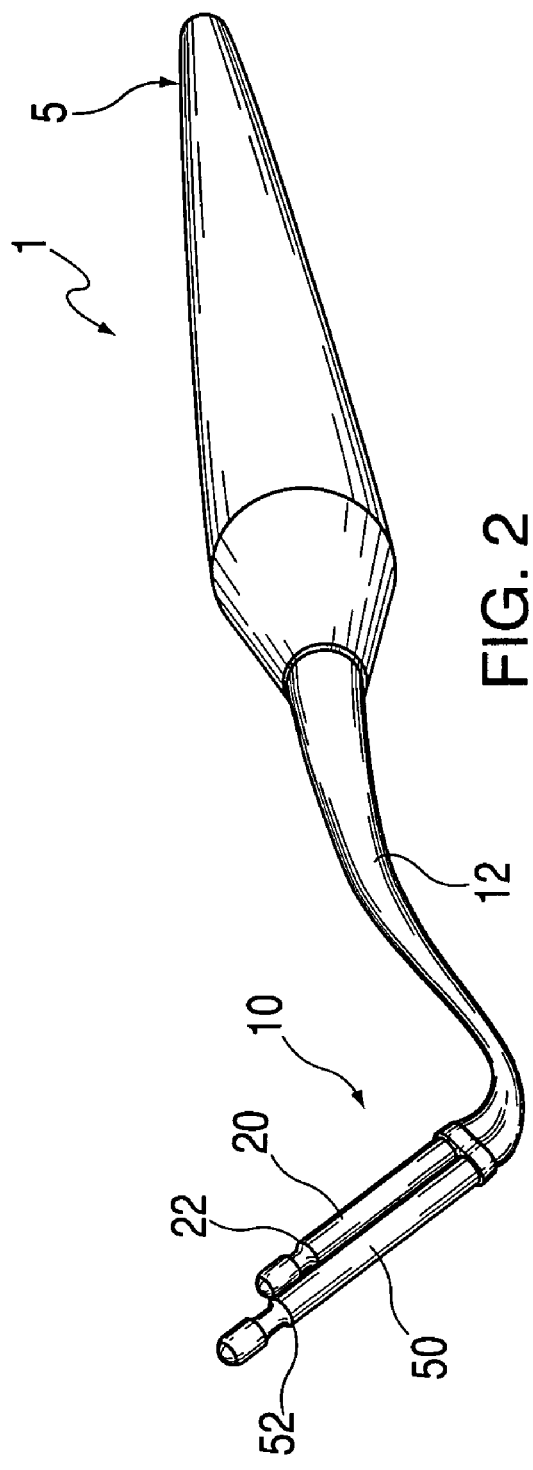

Small

Average

Large

Small

Average

Large

Small

Average

Large

Small

Average

Large

Small

Average

Large

Small

Average

Large

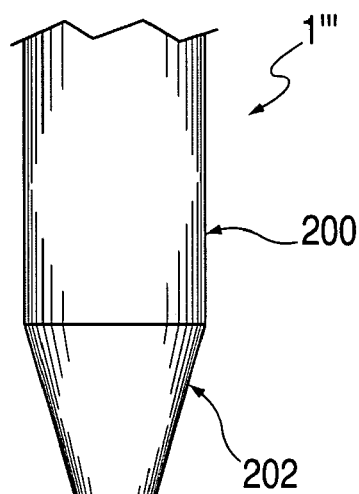
FIG. 18
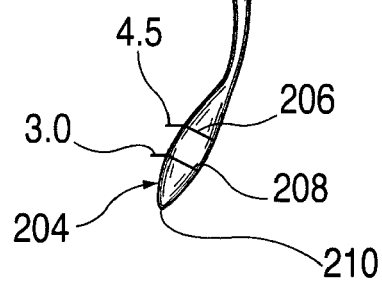
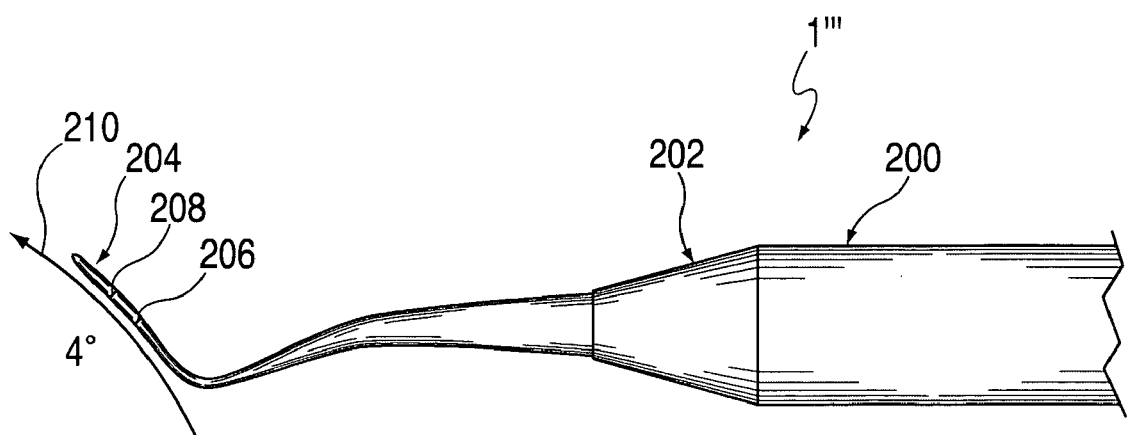
FIG. 19

DENTAL MEASUREMENT INSTRUMENTS

CROSS-REFERENCE TO RELATED APPLICATIONS

This application is a continuation-in-part of U.S. patent application Ser. No. 10/854,667 filed May 26, 2004 now U.S. Pat. No. 7,059,852.

STATEMENT REGARDING FEDERALLY SPONSORED RESEARCH OR DEVELOPMENT

Not applicable.

REFERENCE TO A "SEQUENCE LISTING"

Not applicable.

BACKGROUND OF THE INVENTION

1. Field of the Invention

The present invention relates to dental measurement instruments.

2. Related Art

In the field of aesthetic restorative dentistry, it is highly desirable to take pre-operative measurements in planning the restorative or surgical procedure. In addition, intra-operative measurements are critical in assessing and predicting the aesthetic outcome of the procedure.

In aesthetic dental procedures (and also in reconstructive and restorative dentistry as well) it is desirable to perform restorative and surgical procedures in accordance with aesthetic considerations so that the operative result is not only medically acceptable, but also aesthetically acceptable. Such considerations are based on measurements of the teeth and aesthetic principles based on measurements. In this regard, see, for example, Ward, Daniel H., "Proportional Smile Design Using the Recurring Esthetic Dental (RED) Proportion," Dental Clinics of North America 2001, 45, No. 1, pgs. 143–154 (2001.)

A first exemplary context for such measurements is establishing the proper tooth proportions and length to width dimensions in reconstructive, restorative and aesthetic tooth analysis. There are three structures that compose the smile—the lips, the gingiva, and the teeth. They must have a harmonious relationship with each other for acceptable facial, dentofacial and dental aesthetic appearance to exist. This harmony results if each of these entities is in proper proportion to the other two. Further, the tooth itself must be properly dimensionally proportioned in order to present the most pleasing smile. Tooth dimensions and proportions also guide the clinician during treatment, specifically in designing the restoration of the tooth and in altering the periodontium. Thus, the need exists to achieve proper and accurate tooth dimension and proportion for each clinical situation.

Heretofore, clinical molds were made of teeth for aesthetic analysis, dimensional measurements were taken from these molds or from positives made from such molds, and these measurements were then manipulated by elaborate computer software to determine the appropriate dimensional proportions of the teeth for the desired aesthetic result. Alternatively, direct dimensional measurements were taken from the patient's teeth, the measurements were entered into data charts, and then mathematical calculations were made with this data to produce a set of desired numerical values. In both of these approaches, the clinician would have to take the numerical output and then use that numerical information along with a ruler intraoperatively to guide the surgical procedure. This approach was clumsy and prone to error.

A second exemplary context for dimensional measurements is its application in aesthetic crown lengthening surgical procedures. Previously, this procedure was accomplished through the use of surgical templates that had limited use with respect to assessment of the osseous crest, biologic width requirements, and clinical crown visualization. All three of these parameters must be able to be visualized and assessed simultaneously in order to create the proper aesthetic, restorative, and periodontal relationship for the dental patient. Further, over time wear and tear on the teeth causes compensatory eruption of the tooth in order to allow confronting contact between corresponding upper and lower teeth. This results in a change in the relative placement of the gingival margin. Desirably, in the foregoing instances the relative length of the clinical crown with respect to that of the biological crown is adjusted to preserve or attain a desired dimensional proportion. The biological crown is the part of the tooth from the crest of the bone to the incisal edge. The clinical crown is the part of the tooth from the gum line, or gingival margin, to the incisal edge and is the portion of the tooth that is normally seen.

Since the heretofore-used surgical templates rely on the use of diagnostic casts, wax-ups, and hardened acrylic overlays on tissue models that cannot be representative of the true clinical scenario, they have limited benefits. In addition, they tend not to fit well, are prone to guesstimation, and are relatively expensive. The use of a ruler, particularly intraoperatively, to measure and give proportions is cumbersome and prone to inaccuracy due to eye fatigue.

A third exemplary context for dimensional measurements is its application in the positioning of the interdental papilla in aesthetic surgical procedures. A fourth exemplary context for dimensional measurements is its application in periodontal bone location or 'sounding' in aesthetic surgical procedures. Each of these categories of procedures require careful, precise, and easy measurement.

BRIEF SUMMARY OF THE INVENTION

A dental measurement instrument of the present invention comprises a handle with two ends and with at least one end having a measuring gauge extending from it. In an embodiment of the present invention, the measuring gauge comprises at least two calibrated measurement shafts, each shaft bearing at least one, and preferably a plurality of, calibration indicia, and the calibration indicia on the two shafts being correlated with each other in a specific predetermined mathematical relationship. In another embodiment of the present invention, the measuring gauge comprises a shaft bearing at least one calibration indicia.

BRIEF DESCRIPTION OF THE DRAWINGS

FIG. 1 is a side elevation view of a dental measurement instrument configured in accordance with a first preferred embodiment of the present invention as a tooth proportion instrument;

FIG. 2 is a side elevation view, in perspective, of the dental measurement instrument of FIG. 1;

FIG. 18 is a top plan view of a dental measurement instrument of FIG. 17;

FIG. 19 is a side elevation view, in perspective, a dental measurement instrument of FIG. 17;

DESCRIPTION OF THE PREFERRED EMBODIMENTS

Figure 4:
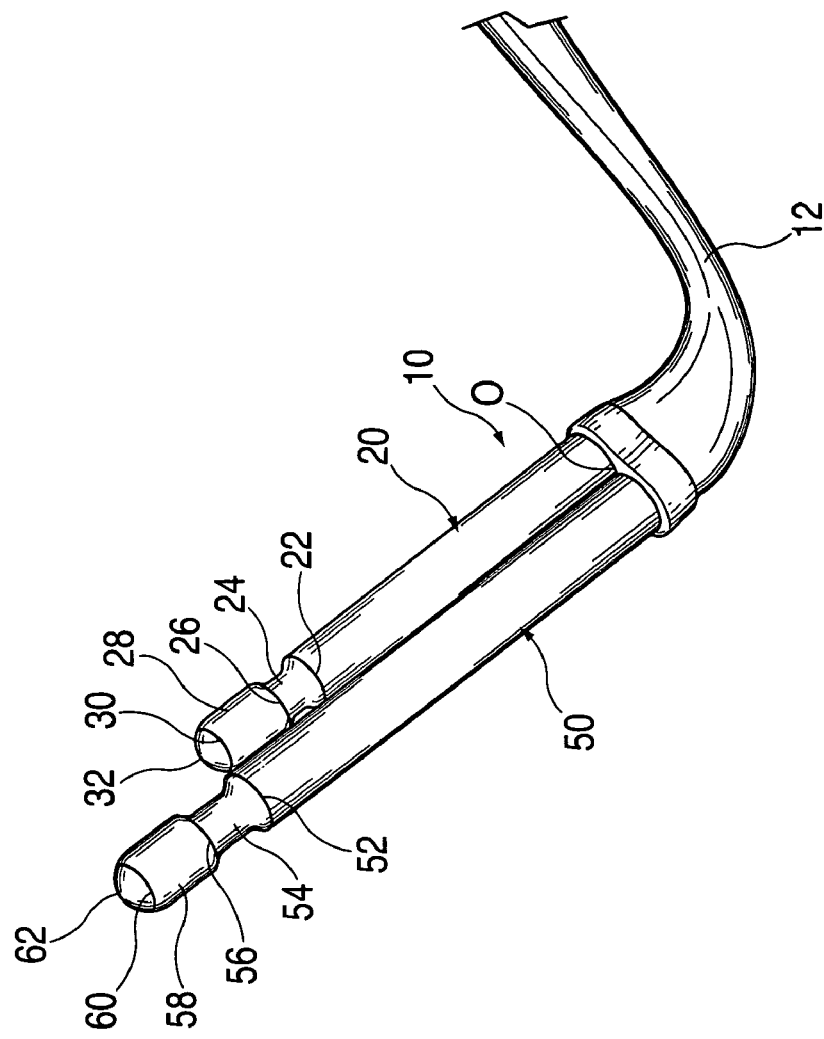
FIG. 4 is a side elevation view, in perspective, on an enlarged scale of an end of the dental measurement instrument of FIG. 1.
Figure 3:
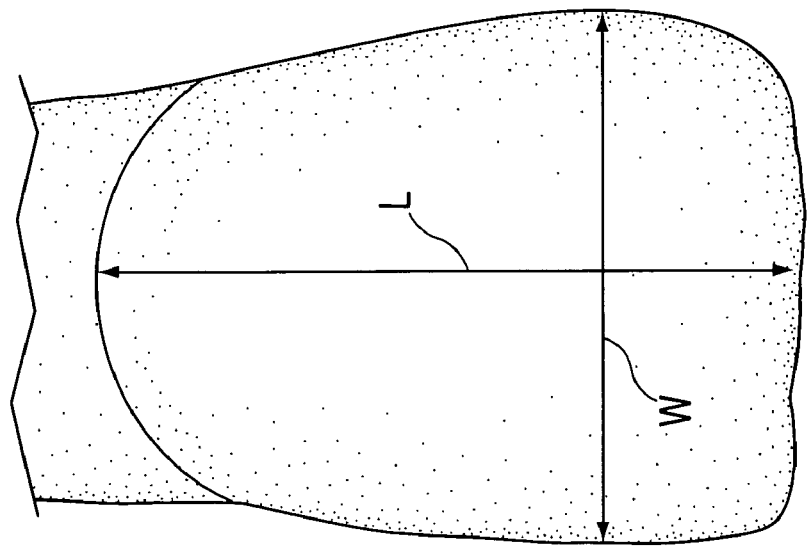
FIG. 3 is a front elevation view of a maxillary central incisor illustrating its width dimension W and its length dimension L.

The dental measurement instruments of the present invention comprise a suite of dental measurement instruments comprising a tooth proportion instrument for aiding in tooth proportion analysis in performing a tooth restorative procedure, a periodontal surgical gauge instrument for aiding in surgical aesthetic crown lengthening procedures, an interdental papilla position instrument for aiding in determining the appropriate position of the interdental papilla of a patient, and a periodontal bone sounding instrument for aiding in determining the location of the osseous crest of a patient in order to preserve biologic width.

The tooth proportion instrument and the periodontal surgical gauge instrument of the present invention each comprise a handle with two ends and with at least one end having a measuring gauge extending from it. In an embodiment, the measuring gauge comprises at least two calibrated measurement shafts, preferably in fixed spatial relationship with each other. Alternatively, the two calibrated measurement shafts may be in pivotable spatial relationship with each other. Each shaft bears at least one, and preferably a plurality of, calibration indicia. The calibration indicia on the two shafts are correlated with each other in a specific predetermined mathematical relationship. Each calibration indicia on one shaft is, preferably, identifiable with respect to a corresponding calibration indicia on the other shaft by identification indicia in accordance with this mathematical relationship. In this way, the physician using the instrument can use a starting measurement using the calibration indicia on one measurement shaft and refer to the corresponding calibration indicia on the second shaft to see or read out the desired outcome of a second measurement. Preferably, the gauge measures distance and the one measurement shaft is used for taking or inputting one distance measurement and the other measurement shaft indicates a second distance as the outcome of the specific predetermined mathematical relationship by an identification indicia on the other measurement shaft that corresponds, by that mathematical relationship, to an identification indicia on the one measurement shaft associated with that one distance. For example, in a tooth restorative procedure, the distances would be tooth width and tooth height; and in a crown lengthening surgical procedure, the distances would be the height of the clinical crown and the height of the biologic crown.

[Tooth Proportion Instrument]

In a first preferred embodiment of the present invention and as shown in FIGS. 1–6, the dental measurement gauge instrument of the present invention may be in the form of a tooth proportion instrument 1 for aiding in tooth proportion analysis in performing a tooth proportioning surgical procedure. The tooth proportion instrument measures tooth length (L) based on tooth width (W.) (See FIG. 3 at W and L.). It has been established that the maxillary anterior teeth, namely the central incisors, lateral incisors and canines, are most aesthetically pleasing when they have a predetermined length to width proportion of about 80%. Alternative designs can incorporate different mathematical ratios.

In such a procedure, in order to reproduce the anatomy of the periodontium apically, pre-operative measurements of the components must be obtained. This is fundamental in resective crown lengthening surgery used to achieve proper tooth proportions and/or positioning the gingival margin relative to the lip. The tooth proportion instrument of the present invention serves to identify tooth disproportion and make the proper corrections whether it is a length issue, a width issue, or both a length and width issue. The length and width of the desired new clinical crown or veneer can then be calculated with the tooth proportion instrument of the present invention. The tooth proportion instrument can be used pre-operatively to take dimensional measurements to plan the procedure and also can be used intra-operatively to evaluate the progress of the procedure.

In the first preferred embodiment of the present invention, the tooth proportion instrument 1 of the present invention comprises a single-ended (or, alternatively, double-ended) handle 5 and with at least one end having a double-headed measuring gauge 10. Preferably, gauge 10 is removable and can be detached to handle 5. The double-head measuring gauge 10 comprises a first calibrated measuring shaft 20 calibrated in dimensional units relevant to periodontal measurements, namely mm. or millimeters, and in a range relevant to the selected patient population for which the tooth proportion instrument is to be used for measuring the width of the tooth and in increments that are relevant to the periodontal procedure for which the instrument is to be used and a second calibrated measuring shaft 50 calibrated in identical units of measure to the first calibrated measuring shaft 10, namely millimeters, and in a range relevant to the selected patient population for which the tooth proportion instrument is to be used for measuring the length of the tooth based on the relevant specific, predetermined mathematical relationship. In the instance of a tooth proportion instrument, this relevant specific, predetermined mathematical relationship is the ratio of the tooth width W to tooth length L. (See FIG. 3 at W and L.). This ratio may also be expressed as a percentage of the length of the tooth and in increments that are relevant to the periodontal procedure. Specifically, the first calibrated measuring shaft 20 is the shorter side of the double-headed, measuring gauge 10 and is calibrated to provide average width dimensions expressed in millimeters and tenths of millimeters of the maxillary anterior teeth (the central incisors, lateral incisors, and canines.) Each shaft 20 and 50 is provided with at least one calibration indicia, such as 22 on the first measuring shaft 20 and 52 on the second measuring shaft 50. Preferably, each shaft 20 and 50 is provided with a plurality of calibration indicia, such as 22, 24, 26, 28, and 30 on the first measuring shaft 20 and a corresponding number of calibration indicia, such as 52, 54, 56, 58, and 60 on the second measuring shaft 50. (See FIG. 4.). In a preferred embodiment and as shown in FIGS. 2 and 4, the calibration indicia may incorporate a plurality of reduced diameter cylindrical grooves spaced at predetermined intervals along the distal end of the measuring shaft to provide alternating original diameter and reduced diameter bands. Alternatively, alternating bands of color or other indicia can be used. (FIGS. 2 and 4 illustrate a measuring gauge 10 with a number of indicia for exemplary purposes.). As shown in FIG. 4 and with respect to the first measuring shaft 20, the first calibration indicia 22 is disposed at the vertex between the original diameter of the measuring shaft 20 and the proximal end of the first reduced diameter groove 24. This indicia 22 represents the distance from the origin point O of the first measuring shaft 20 to this vertex, or the first calibration indicia 22. The origin point O is provided by a circumferential band that circumscribes the merge of the shafts 20 and 50 with shank 12. The origin point may also be provided by a mark, such as a colored stripe. The third calibration indicia 26 is disposed at the vertex between the original diameter of the measuring shaft 20 and the distal end of the first reduced diameter groove 24. This indicia 26 represents the distance from the origin point O of the first measuring shaft 20 to this vertex, or the third calibration indicia 26. The first reduced diameter groove 24 also provides a second calibration indicia 24 represents a range of distances, starting with the distance from the origin point O to the first vertex 22 and ending with the distance from the origin point O to the second vertex 26. Similarly, the fifth calibration indicia 30 is disposed at the vertex between the original diameter of the measuring shaft 20 and the curved tip 32 of the shaft 20. This indicia 30 represents the distance from the origin point O of the first measuring shaft 20 to this vertex, or the fifth calibration indicia 30. The first original diameter band 28 between reduced diameter groove 24 and the tip 32 provides a fourth calibration indicia 28 that represents a range of distances, starting with the distance from the origin point O to the second vertex 26 and ending with the distance from the origin point O to the third vertex 30. The tip 32 also provides a tenth calibration indicia 32 that represents the distance from the origin point O to the end of the tip 32. The same configurational relationships apply to the calibration indicia 52–62 of the second measuring shaft. However, each distance on the second measuring shaft 50 represents a specific predetermined mathematically related distance with respect to the respective corresponding distance on the first measuring shaft 20.

In using the instrument 1 the dental professional would measure the tooth width using either a ruler or the calibration indicia on the first measuring shaft 20 and select a calibration indicia that corresponded to and represented the width of the tooth being evaluated and restored, selecting say the third calibration indicia 26 on the first measuring shaft as accurately representing the width of the tooth. In analyzing and proportioning the length of that same tooth, the dental professional would refer to the third calibration indicia on the second measuring shaft 50. In this way the given tooth width dimension is translated into the desired tooth length dimension via the specific, predetermined mathematical relationship, namely the width to length ratio.

Figure 5A:
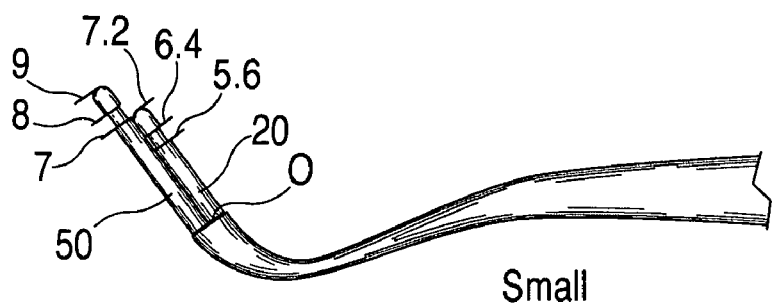
FIG. 5A is a side elevation view of an end of a dental measurement instrument of FIG. 1 for measuring small maxillary anterior teeth.
Figure 5B:
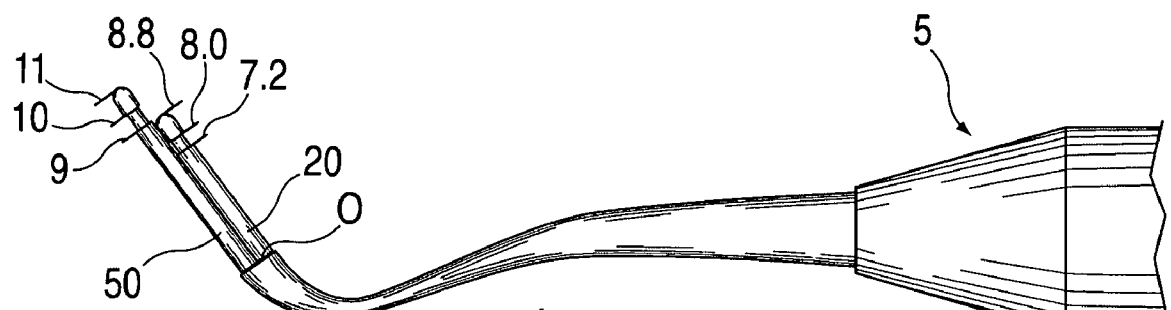
FIG. 5B is a side elevation view of an end of a dental measurement instrument of FIG. 1 for measuring average maxillary anterior teeth.
Figure 5C:
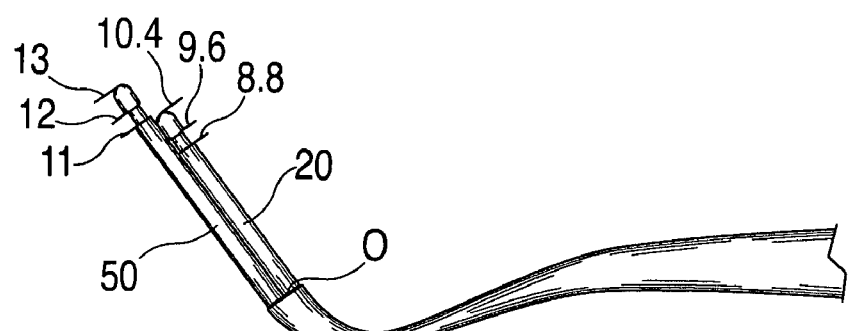
FIG. 5C is a side elevation view of an end of a dental measurement instrument of FIG. 1 for measuring large maxillary anterior teeth.
Figure 6A:
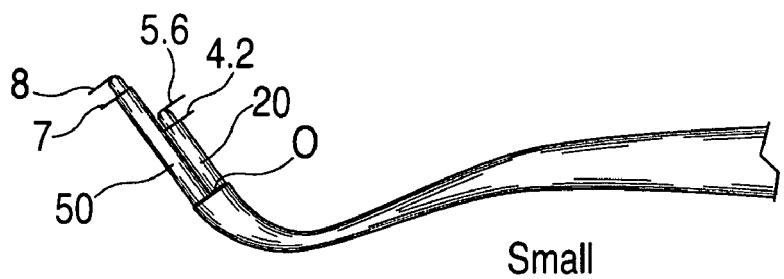
FIG. 6A is a side elevation view of an end of a dental measurement instrument of FIG. 1 for measuring small mandibular anterior teeth.
Figure 6B:
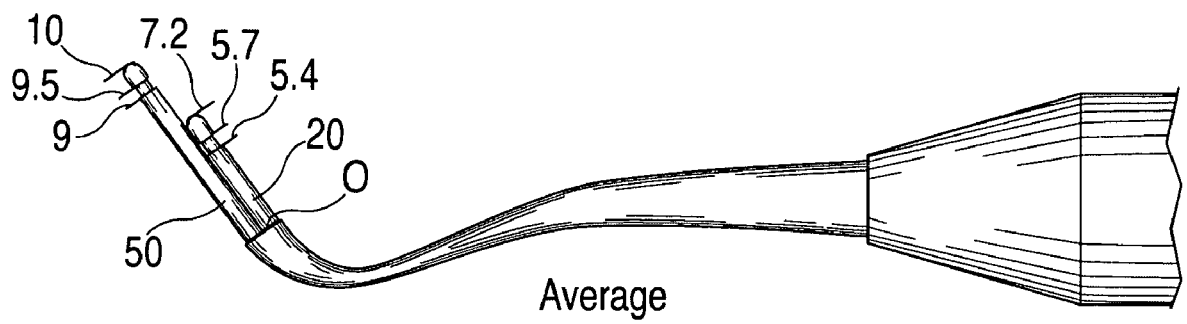
FIG. 6B is a side elevation view of an end of a dental measurement instrument of FIG. 1 for measuring average mandibular anterior teeth.
Figure 6C:
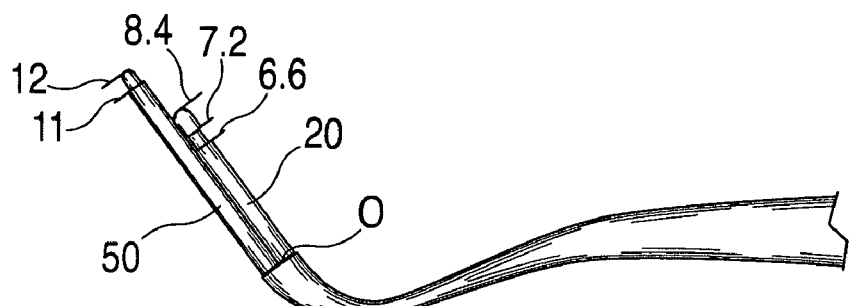
FIG. 6C is a side elevation view of an end of a dental measurement instrument of FIG. 1 for measuring large mandibular anterior teeth.
Figure 7:
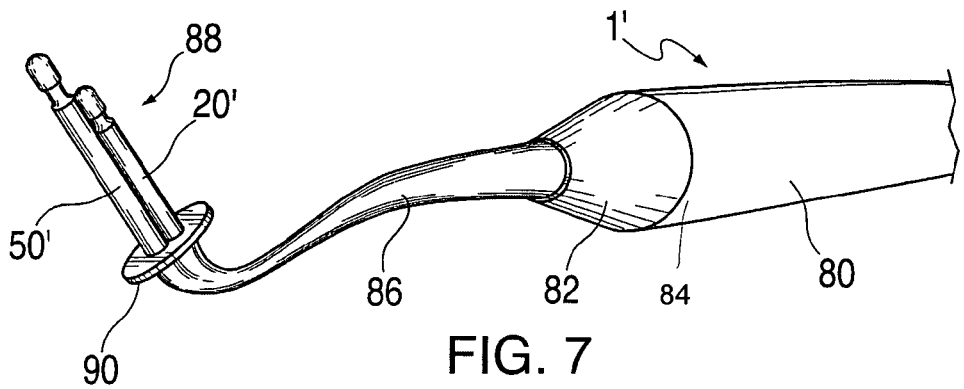
FIG. 7 is a side elevation view, in perspective, of a dental measurement instrument configured in accordance with a second preferred embodiment of the present invention as a periodontal surgical gauge instrument.

The correspondence between tooth width dimension, or distance, as measured or input on the first measuring shaft 20 and tooth length dimension, or distance, as measured or read out on the second measuring shaft 50 where the mathematical relationship is the ratio between the two dimensions is illustrated in FIGS. 5A–5C for maxillary anterior teeth and FIGS. 6A–6C for mandibular anterior teeth where the width to length ratio (expressed as a percentage) is 80%. (Study has indicated that this percentage is optimum for a satisfactory aesthetic result. Other desired width to length ratios may be adapted to the present invention.) For example, the width numerical values of 5.6 mm, 6.4 mm, and 7.2 mm are translated into the desired length numerical values of 7 mm, 8 mm, and 9 mm. for small anterior mandibular teeth in FIG. 5A. The dimensions indicated on FIGS. 5A–5C and 6A–6C are in mm.

Preferably, each tooth width dimension, or distance, on the first calibrated measuring shaft 20 is color-coded and the corresponding recommended tooth length dimension, or distance, on the second calibrated measuring shaft 50 is color-coded with the same color. The length dimensions are provided in millimeters on the longer side of the double-headed measuring gauge 10, i.e., the second calibrated measuring shaft 50, and are representative of the desired length dimensions of the anterior teeth. (See FIGS. 5A for small anterior mandibular teeth, 5B for average anterior mandibular teeth, 5C for large anterior mandibular teeth, 6A for small anterior maxillary teeth, 6B for average anterior maxillary teeth, and 6C for large anterior maxillary teeth.).

The device 1 may be provided in two forms: one as a maxillary proportion tool for use in proportioning analysis of the maxillary dentition and the second as a mandibular proportion tool for use in proportioning analysis of the mandibular dentition. The mandibular proportion tool may be configured with the same preset standards provided for length, width and proportion ratios. (See FIGS. 5A–5C and 6A–6C, respectively.).

The handle may comprise an elongated cylindrical grip provided with a series of circumferential relief grooves to enhance gripping and a tapered transition at the operative end. Extending from the tapered transition at least at one end is an integral narrow support shank 12. The measuring gauge 10 extends distally from the support shank 12 and comprises a set of at least two calibrated measurement shafts 20 and 50. The at least two calibrated measurement shafts 20 and 50 are in fixed relationship to each other and, preferably, attached to each other in side-by-side relationship. The support shank 12 extends from the handle to the calibrated measurement shafts in an extended S-shaped curve that serves to align (a) the handle and (b) the calibrated measurement shafts with respect to each other so that the two calibrated measurement shafts 20 and 50 can be placed against a tooth for width or length measurement with the handle 5 being in a comfortable orientation for the user. The calibrations on the two shafts 20 and 50 are correlated with each other in a mathematical relationship and identifiable by indicia in accordance with this mathematical relationship. Optionally, the at least two calibrated measurement shafts may be provided with a transverse band at the intersection of the two calibrated measurement shafts 20 and 50 with the support shank 12 to facilitate measurement, the band acting as an abutment against the tooth under consideration or analysis.

It has been found that it is preferable to refine the dimensional relationships further by providing small, average and large sizing ranges. A "small" range represents patients having anterior tooth length of 7–9 mm. An "average" range represents patients having anterior tooth length of 9–11 mm. A "large" range represents patients having anterior tooth length of 11–13 mm. Further, by dividing the patient population into these ranges, it is possible to define:

(1) a single numerical value for the width (and, therefore, length) of the central incisors;

(2) a single numerical value for the width (and, therefore, length) of the lateral incisors; and (3) a single numerical value for the width (and, therefore, length) of the canines;

of the patient receiving treatment. The relevant distances for maxillary anterior teeth, expressed in millimeters, are illustrated in FIGS. 5A for the small category, 5B for the average category, and 5C for the large category and are set forth in the following Table 1:

TABLE 1

| | MAXILLARY JAW | | | | | |
|---|---|---|---|---|---|---|
| | SIZE | | | | | |
| | SMALL | | AVERAGE | | LARGE | |
| TOOTH | WIDTH | LENGTH | WIDTH | LENGTH | WIDTH | LENGTH |
| Lateral Incisor | 5.6 | 7 | 7.2 | 9 | 8.8 | 11 |
| Canine | 6.4 | 8 | 8.0 | 10 | 9.6 | 12 |
| Central Incisor | 7.2 | 9 | 8.8 | 11 | 10.4 | 13 |

The relevant distances for mandibular anterior teeth, expressed in millimeters, are illustrated in FIGS. 6A for the small category, 6B for the average category, and 6C for the large category and are set forth in the following Table 2:

TABLE 2

| | MANDIBULAR JAW | | | | | |
|---|---|---|---|---|---|---|
| | SIZE | | | | | |
| | SMALL | | AVERAGE | | LARGE | |
| TOOTH | WIDTH | LENGTH | WIDTH | LENGTH | WIDTH | LENGTH |
| Central Incisor | 4.2 | 7 | 5.4 | 9 | 6.6 | 11 |
| Lateral Incisor | 4.2 | 7 | 5.7 | 9.5 | 7.2 | 12 |
| Canine | 5.6 | 8 | 7.2 | 10 | 8.4 | 12 |

Because of the morphology and typical dimensions of the mandibular central and lateral incisors of small patients, only a single numerical value for the central and lateral incisors need be given for width (and, therefore, length) for these patients.

In an alternative form of the first preferred embodiment of the present invention, the tooth proportion instrument 1a of the present invention comprises a single-ended (or, alternatively, double-ended) handle 5a and with at least one end having a double-headed measuring gauge 10a. (Measuring gauge 10a may be removable and can be detached from handle 5a.) The double-head measuring gauge 10a comprises a first calibrated measuring shaft 20a for measuring the width of a tooth and a second calibrated measuring shaft 50a for measuring the length of the tooth. The first calibrated measuring shaft 20a is calibrated in mm. or millimeters, and in a range relevant to the selected patient population for which the tooth proportion instrument is to be used for measuring the width of the tooth, and in increments that are relevant to the tooth restorative procedure for which the instrument is to be used. The second calibrated measuring shaft 50a is calibrated in identical units of measurement to the first calibrated measuring shaft 10a, namely millimeters, and in a range relevant to the selected patient population for which the tooth proportion instrument is to be used for measuring the length of the tooth based on the relevant specific, predetermined mathematical relationship. In the instance of a tooth proportion instrument, this relevant specific, predetermined mathematical relationship is the ratio of the tooth width W to tooth length L. (See FIG. 3 at W and L.). This ratio may also be expressed as a percentage of the length of the tooth and in increments that are relevant to the periodontal procedure. Specifically, the first calibrated measuring shaft 20a is calibrated to provide average width dimensions expressed in millimeters and tenths of millimeters of the maxillary anterior teeth (the right and left central incisors, right and left lateral incisors, and right and left canines.) Each shaft 20a and 50a is provided with at least one calibration indicia, such as 22a on the first measuring shaft 20a and 52a on the second measuring shaft 50a. (FIGS. 28–31 illustrate a measuring gauge 10a with a number of indicia for exemplary purposes.) Preferably, each shaft 20a and 50a is provided with a plurality of calibration indicia, such as 22a, 24a, 26a, 28a, 30a, and 32a on the first measuring shaft 20a and a corresponding number of calibration indicia, such as 52a, 54a, 56a, 58a, 60a, and 62a on the second measuring shaft 50a. (See FIG. 28.). In a preferred embodiment and as shown in FIGS. 28–31, the calibration indicia may incorporate a plurality of alternating bands of color. Alternatively, other indicia or a set of reduced diameter cylindrical grooves spaced at predetermined intervals along the distal end of the measuring shaft to provide alternating original diameter and reduced diameter bands can be used. Calibration indicia 22a, 26a and 30a on the first calibration shaft 20a and calibration indicia 52a, 56a and 60a on the second calibration shaft 50a are color-coded bands that each represent a distance range. Calibration indicia 24a, and 28a on the first calibration shaft 20a and calibration indicia 54a, and 58a on the second calibration shaft 50a are the intersections or junctures between color-coded bands that each represent a specific distance. Calibration indicia 32a on the first calibration shaft 20a and calibration indicia 62a on the second calibration shaft 50a are the terminal edges of the last color-coded band that each represent a specific distance.

The handle 5a may comprise an elongated cylindrical grip as previously described and a tapered transition at the operative end. Extending from the tapered transition at least at one end is an integral narrow support shank 12a. The measuring gauge 10a extends distally from the support shank 12a and comprises a set of at least two calibrated measurement shafts 20a and 50a. The at least two calibrated measurement shafts 20a and 50a may be in fixed relationship to each other or, alternatively, may be pivotably mounted with respect to each other. The support shank 12a extends from the handle 5a to the calibrated measurement shafts 20a and 50a in an extended S-shaped curve that serves to align (a) the handle and (b) the calibrated measurement shafts 20a and 50a with respect to each other so that the two calibrated measurement shafts 20a and 50a can be placed against a tooth for width or length measurement with the handle 5a being in a comfortable orientation for the user. The calibrations on the two shafts 20a and 50a are correlated with each other in a mathematical relationship and identifiable by indicia in accordance with this mathematical relationship.

Figure 28:
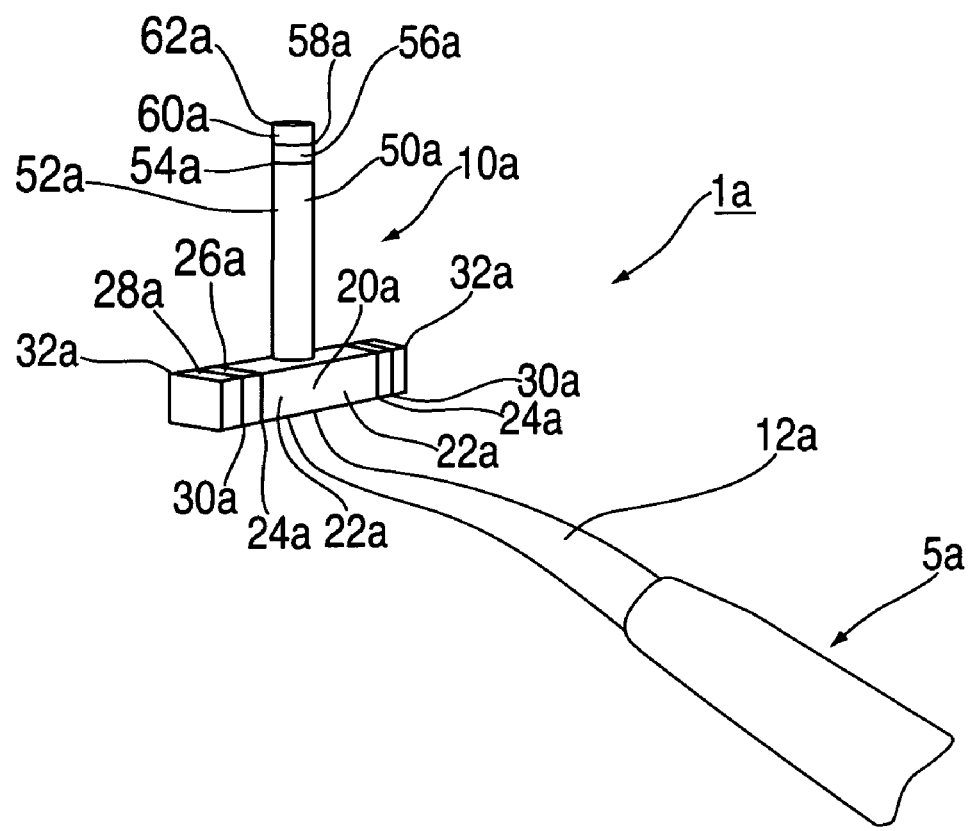
FIG. 28 is a side elevation view, in perspective, of a dental measurement instrument configured in accordance with an alternative form of the first preferred embodiment of the present invention as a tooth proportion instrument.

As shown in FIG. 28 and with respect to the first measuring shaft 20a and the second measuring shaft 50a, the first and second measuring shafts 20a and 50a are joined at right angles in an inverted T-shaped configuration with the first measuring shaft 20a extending transversely of the shank 12a of an end of the handle 5a and of the second measuring shaft 50a on both sides of the second measuring shaft 50a and with the second measuring shaft 50a extending vertically upwardly from the transversely extending first measuring shaft 20a. Preferably, the first calibrated measurement shaft 20a acts as an abutment against the tooth under consideration or analysis. Also preferably, the second measuring shaft 50a extends vertically upwardly from the midpoint of the first measuring shaft 20a so that each end extremity of the first measuring shaft 20a extends generally equidistantly on each side of the second measuring shaft 50a. The first measuring shaft 20a is a rectilinear bar that is square in cross-section so that it presents a straight, flat edge to the tooth that is being measured. The second measuring shaft 50a is cylindrical so that it presents a curved surface to the tooth that is being measured for ease of measurement.

Further, as shown in FIG. 28 and with respect to the first measuring shaft 20a, the first calibration indicia 22a is a central band that extends on each side of the second measuring shaft 50a. This indicia 22a represents a first distance range for measurement of tooth width. The indicia 22a is a circumferential color-coded band of predetermined length. The third calibration indicia 26a is a pair of circumferential color-coded band, of a different color from indicia 22a, each being of equal, predetermined length. The width of these bands (indicia 24a) and the indicia 22a, in aggregate represents a second distance range for measurement of tooth width. The junction or intersection between indicia 22a and each of indicia 26a provides a second calibration indicia 24a that represents a first specific distance. Similarly, the fifth calibration indicia 28a is a pair of circumferential color-coded bands (of a different color from indicia 22a and 24a) each being of equal, predetermined length. The width of these bands (indicia 28a) and the indicia 22a and 24a, in aggregate represents a third distance range for measurement of tooth width. The junction or intersection between each of indicia 26a and each of adjacent indicia 28a provides a fourth calibration indicia 30a that represents a second specific distance. Finally, the opposed distal ends of the first measurement shaft 20a provide a fifth calibration indicia 32a that represents a third specific distance.

The same configurational relationships apply to the calibration indicia 52a–62a of the second measuring shaft. However, each distance on the second measuring shaft 50a represents a specific predetermined mathematically related distance with respect to the respective corresponding distance on the first measuring shaft 20a. In other words, a measured tooth width falling within the range represented by indicia 26a should have a desired, or outcome, tooth length falling within the range represented by indicia 56a. Similarly, a measured tooth width falling on the juncture or intersection represented by indicia 24a should have a desired, or outcome, tooth length falling on the juncture or intersection represented by indicia 54a.

In using the instrument 1a the dental professional would measure the tooth width using the calibration indicia on the first measuring shaft 20a and select a calibration indicia that corresponded to and represented the width of the tooth being evaluated and restored, selecting say the third calibration indicia 26a on the first measuring shaft 20a as accurately representing the width of the tooth. In analyzing and proportioning the length of that same tooth, the dental professional would refer to the third calibration indicia on the second measuring shaft 50a, i.e. calibration indicia 56a. In this way, the given tooth width dimension is translated into the desired tooth length dimension via the specific, predetermined mathematical relationship, namely the width to length ratio. The advantage of the inverted T-bar configuration of this form of the first embodiment is that the dental professional is able to keep the measuring gauge 10a in the same orientation for both tooth width measurement and tooth length readout or comparison, thereby making the use of the instrument and the technique easier and more likely to be used effectively. In addition, in the alternative form of the first embodiment where the second measurement shaft 50a is pivotable with respect to the first measurement shaft 20a, the dental professional can more easily measure and work on teeth that are themselves crooked or crooked in orientation. In this form the first measurement shaft 20a can be aligned transversely on the tooth in whatever form or orientation the tooth is in for optimum tooth width measurement while the pivotable second measurement shaft 50a can be pivoted to align with the lengthwise axis of the tooth and the readout can be made along the appropriate axis rather than taking the measurement with the first measurement shaft transversely aligned to the tooth and then reorienting the device 1a for reading out the tooth length in a second orientation dictated by the aberration of the tooth.

Figure 29:
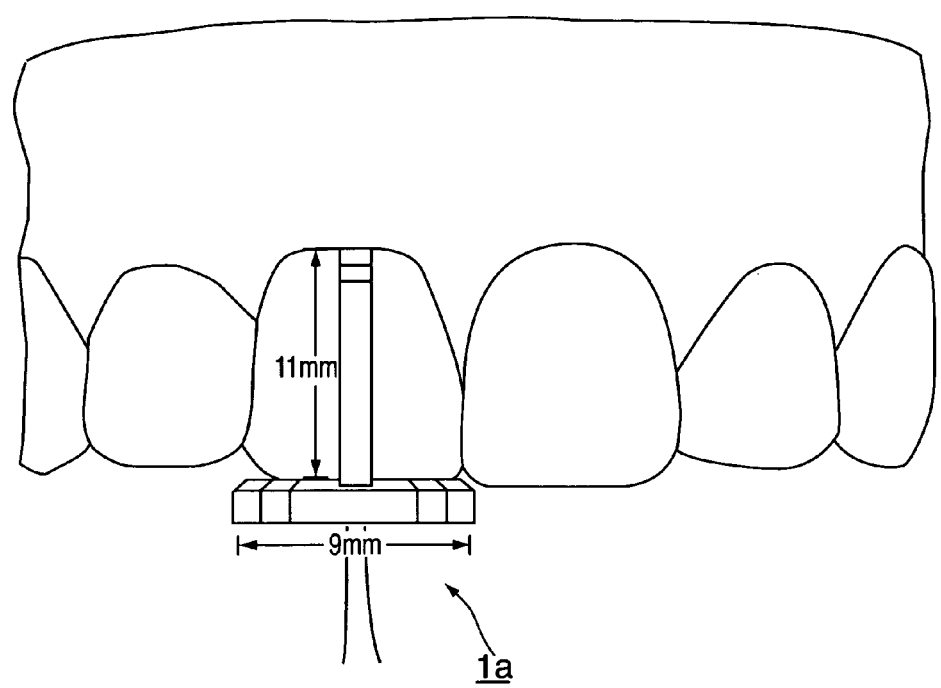
FIG. 29 is a front elevation view of an end of the dental measurement instrument of FIG. 28 illustrating measurement with respect to a right maxillary central incisor.
Figure 30:
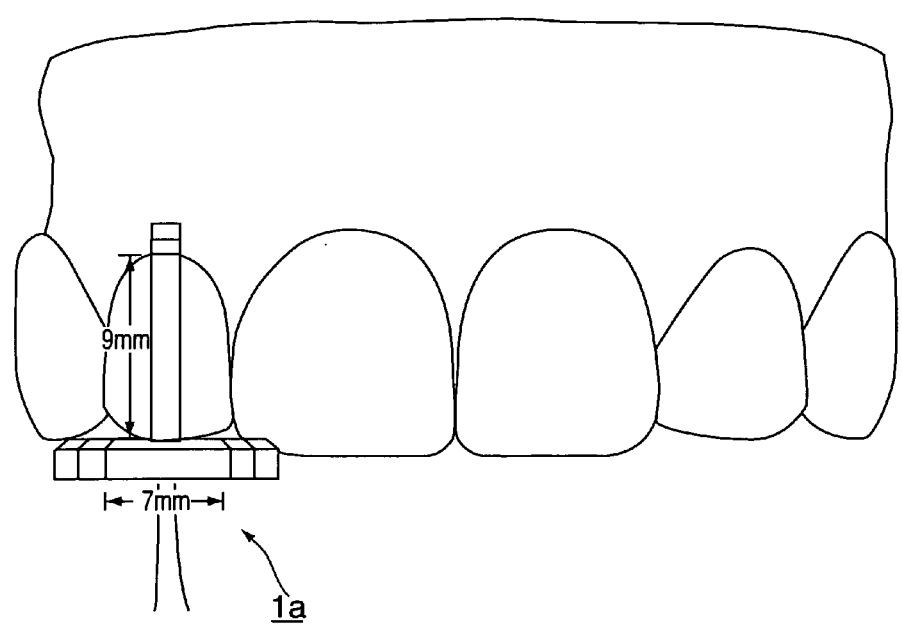
FIG. 30 is a front elevation view of an end of the dental measurement instrument of FIG. 28 illustrating measurement with respect to a right maxillary lateral incisor.
Figure 31:
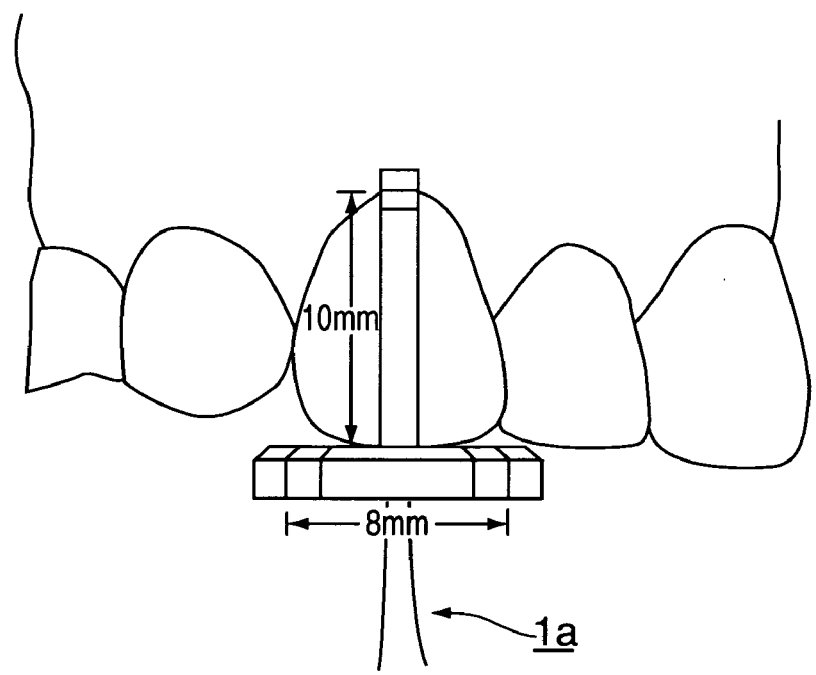
FIG. 31 is a front elevation view of an end of the dental measurement instrument of FIG. 28 illustrating measurement with respect to a right maxillary canine.

The correspondence between tooth width dimension, or distance, as measured or input on the first measuring shaft 20a and tooth length dimension, or distance, as measured or read out on the second measuring shaft 50a where the mathematical relationship is the ratio between the two dimensions is illustrated in FIGS. 29–31 for maxillary anterior teeth. where the width to length ratio (expressed as a percentage) is 80%. (Study has indicated that this percentage is optimum for a satisfactory aesthetic result. Other desired width to length ratios may be adapted to the present invention.) For example, the width numerical values of 7 mm (FIG. 30), 8 mm (FIG. 31), and 9 mm (FIG. 29) are translated into the desired length numerical values of 9 mm, 10 mm, and 11 mm. for anterior maxillary teeth in FIGS. 29–31. (The dimensions indicated on FIGS. 29–31 are in mm.)

Preferably, each tooth width dimension, or distance, on the first calibrated measuring shaft 20a is color-coded and the corresponding recommended tooth length dimension, or distance, on the second calibrated measuring shaft 50a is color-coded with the same color. The length dimensions are provided in millimeters on the longer side of the double-headed measuring gauge 10a, i.e., the second calibrated measuring shaft 50a, and are representative of the desired length dimensions of the anterior teeth. (As in the embodiments of FIGS. 5A–5C and 6A–6C, the width and length dimensions for this alternative form of the first embodiment can be encoded on the first and second measuring shafts for small anterior mandibular teeth (see FIG. 5A), average anterior mandibular teeth (see FIG. 5B), large anterior mandibular teeth (see FIG. 5C), small anterior maxillary teeth (see FIG. 6A), average anterior maxillary teeth (see FIG. 6B), and large anterior maxillary teeth (see FIG. 6C).)

The device 1a may be provided in two forms: one as a maxillary proportion tool for use in proportioning analysis of the maxillary dentition and the second as a mandibular proportion tool for use in proportioning analysis of the mandibular dentition. The mandibular proportion tool may be configured with the same preset standards provided for length, width and proportion ratios, such as may be done for the other form of the first embodiment, see FIGS. 5A–5C and 6A–6C, respectively, for guidance.

[Periodontal Surgical Gauge Instrument]

In a second preferred embodiment of the present invention and as shown in FIGS. 7–11, and 16, the dental measurement instrument of the present invention may be in the form of a measurement tool for aiding in performing a crown lengthening surgical procedure for adjusting the relative length of the clinical crown with respect to the length of the biological crown. (The length of the clinical crown is the height of the apex of the tooth from the gingival margin and may be conceptualized as the visual height of the tooth. The length of the biological crown is the height of the apex of the tooth from the intersection of the tooth with the osseous crest of the bone within which the tooth is embedded and may be conceptualized as the visual height of the tooth if all nonosseous tissue were removed from view.).

In altered passive eruption, placing the gingival margin at the cemento enamel junction (CEJ), thereby exposing the anatomic crown, gingivectomy-gingivoplasty or a flap can be performed. In both techniques the incision is made at the desired point of the future gingival margin.

Relative to managing the soft tissue in situations where the entire zone of keratinized tissue resides on the anatomic crown, placement of the incision at the CEJ performing either a gingivectomy or a flap, would result in an inadequate amount of attached gingiva. To preclude creating this deficiency, the mucogingival junction must be located at or apical to the osseous crest. In these instances a full or split thickness flap is elevated and the margin is positioned at the CEJ. The mucogingival junction as a result will be apical to the osseous crest.

Certain esthetic deformities that involve excessive gingival display may require a modification of the resective osseous surgery described above. In these situations merely exposing the anatomic crown would not sufficiently reduce the gingival display nor permit the creation of the proper tooth size and position. Positioning the gingival margin apically on the root surface is performed to increase the clinical crown's inciso-apical dimension or to place the gingival margin in a more favorable position relative to the upper lip.

In treating these case types the fundamental objectives and considerations associated with resective surgery remain the same. Once the desired position of the gingival margin is defined the surgeon can establish the osseous crest sufficiently apical to this point to accommodate the biologic width and crevicular space. Moreover the periodontal architecture is recreated apically. Furthermore, to ensure an adequate zone of attached gingiva the soft tissue is positioned apically so that the mucogingival junction is apical to the osseous crest.

The facial surface can be treated exclusively if the apico-incisal position of the contact areas will remain the same and the interdental tissue volume is not excessive. However, if the contact areas are to be positioned apically, the height of the interproximal septum needs to be reduced. In addition, limiting treatment to the facial surface assumes that the lingual tissue margin is located in the vicinity of the CEJ and the crevicular depth can be maintained in health.

The dental measurement instrument of the second preferred embodiment of the present invention is useful in planning and performing the foregoing surgical procedures and provides an alternative to the use of surgical templates. It is particularly helpful since, in the context of this surgical procedure, the clinician does not have a landmark to use as a guide in measuring the new position of the osseous crest in reference to the length of the new clinical crown. The dental measurement instrument of this embodiment can also be used in situations of apical repositioning of the surgical flap when an inadequate zone of attached gingival tissue exists preoperatively. The biologic crown needs to be visualized and the draped flap does not allow this to occur. (The biologic crown is defined as the clinical crown plus the biologic width.).

The dental measurement instrument of the second preferred embodiment is particularly helpful in this scenario since the clinician does not have a landmark to use as a guide in measuring the new position of the osseous crest in reference to the length of the new clinical crown. This is because the location of the CEJ serves as a landmark and is altered due to the compensatory eruption of the tooth in a more incisal spatial orientation. In contrast to altered passive eruption cases (APE), the CEJ is a helpful landmark and serves as a reference point when exposing the anatomic crown. (The tooth proportion instrument of the first preferred embodiment tool is more helpful in the APE case type.). The dental measurement instrument of the second preferred embodiment is designed to be used in conjunction with the tooth proportion instrument of the first preferred embodiment tool since the proper tooth proportion ratio must be established first. The length of the desired and new clinical crown can then be calculated with the dental measurement instrument of the second embodiment.

The dental measurement instrument of the second preferred embodiment tool is designed to facilitate aesthetic crown lengthening procedures and is an alternative method to the use of surgical templates which may have limited use in the assessment of the osseous crest, biologic width requirements, and clinical crown visualization. All three parameters must be able to be visualized and assessed simultaneously in order to create the proper aesthetic, restorative, and periodontal relationship. Since surgical templates rely on the use of diagnostic casts, wax-ups, and hardened acrylic overlays on tissue models that cannot be representative of the true clinical scenario, they have limited benefits. The dental measurement instrument of the present invention is also helpful in situations of apical repositioning of the surgical flap when an inadequate zone of attached gingival tissue exists preoperatively. When an adequate zone exists, the tooth borders or margins of the flap can be used to help measure the clinical crown but again the biologic crown needs to be visualized and the draped flap does not allow this to occur.

The dental measurement instrument of the second preferred embodiment requires that the incisal edge must be established prior to its use. If aberrations in the incisal plane exist, correction can easily be made through the use of an intraoral composite 'mock-up' procedure prior to surgery.

A 1.0 mm tissue discrepancy in reference to the predictability of the presence or absence of the interdental papilla is important and clinically significant. It is not uncommon in the attrition case type that the interproximal tissue is also too incisal and repositioning of the interdental papilla is a requisite. A 1.0 mm discrepancy is also true in reference to tooth proportions and length of the mid-facial crest of tissue. A 1.0 mm discrepancy would equal 10% of the clinical crown height of a 10.0 mm tooth and a decrease in tooth proportion from 80% to 72% making the final appearance of the tooth to be too narrow.

The periodontal surgical gauge instrument of the second preferred embodiment comprises a double-headed measurement instrument with one end bearing the aforesaid double-head. The double-head is used to measure the height of the position of the new clinical crown and the height of the position of the biologic crown simultaneously. The shorter side of the double-headed end of the instrument is used to locate the height of the new clinical crown and the longer side the height of the biologic crown. These parameters (clinical crown height and biologic crown height) must be able to be visualized by the surgeon simultaneously during the surgical process in order to ensure proper aesthetic tooth proportion. (The other end of the instrument may be used to orient the position of the new papilla location as discussed later since frequently the position of the interdental papilla is skewed as well.). Moving the osseous crest too far apically can lead to a disproportionate and excessive clinical crown length or an unstable mid-facial free gingival margin. Insufficient removal of osseous crest tissue can lead to inadequate clinical crown length or subsequent violation of biologic width during tooth preparation. These concepts are important since normal anatomic landmarks may not be present. New mid-facial tissue and interproximal papilla must be re-established and created for these patients. As with the tooth proportion instrument of the first embodiment, the periodontal surgical gauge instrument of the second embodiment may be provided either in the form of an instrument for the maxillary jaw or in the form of an instrument for the mandibular jaw.

As may be seen in FIGS. 7–11, the handle of the periodontal surgical gauge instrument 1' may comprise an elongated cylindrical handle 80 with a tapered transition 82 at one end 84. (Optionally, the handle 80 may be provided with a series of circumferential relief grooves to enhance gripping.). Extending from the tapered transition 82 at one end is an integral narrow support shank 86. A crown-measuring gauge 88 (FIG. 7) extends distally from the support shank 86 and comprises a set of at least two calibrated measurement shafts 20' and 50'. Preferably, gauge 88 is removably attached to handle 80 that at least two calibrated measurement shafts 20' and 50' are in fixed relationship to each other and, preferably, attached to each other in side-by-side relationship. The support shank 86 extends from the handle to the measuring gauge 88 and the calibrated measurement shafts 20' and 50' in an extended S-shaped curve that serves to align (a) the handle and (b) the calibrated measurement shafts 20' and 50' with respect to each other so that the two calibrated measurement shafts 20' and 50' can be placed against a tooth for clinical crown and biological crown measurement with the handle being in a comfortable orientation for the user. The calibrations on the two shafts 20' and 50' are correlated with each other in a specific, predetermined mathematical relationship and identifiable by indicia in accordance with this mathematical relationship. In the instance of the periodontal surgical gauge of the present invention this mathematical relationship is a fixed distance positive offset of the length of the biological crown from the length of the clinical crown. For anterior maxillary teeth this offset is a +3 mm. and for anterior mandibular teeth it is a +2.5 mm. This offset permits the tissue to re-establish itself providing about 1 mm. for connective tissue, 1 mm. for junctional epithelium and 1 mm. for periodontal pocket depth for maxillary teeth. Proportions for mandibular teeth, since they have a thinner base and a tendency for gum recession, would need additional compensation because mandibular bone and gum tissue are very delicate.

The two calibrated measurement shafts 20' and 50' may be provided with a transverse stop collar 90 at the intersection of the two calibrated measurement shafts 20' and 50' with the support shank 86 to facilitate measurement, the collar 90 acting as an abutment against the tooth under consideration or analysis. The stop collar 90 may be circular or oval in top plan.

Figure 8A:
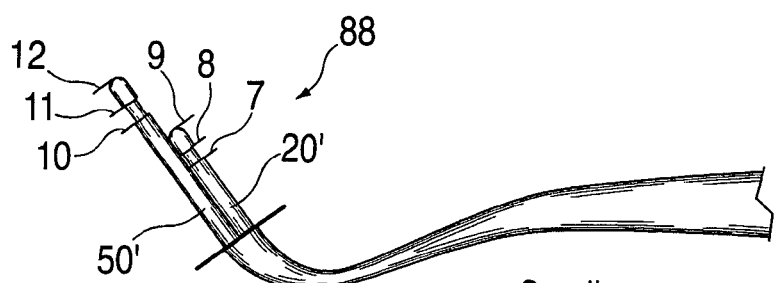
FIG. 8A is a side elevation view of an end of a dental measurement instrument of FIG. 7 for measuring small maxillary teeth.
Figure 8B:
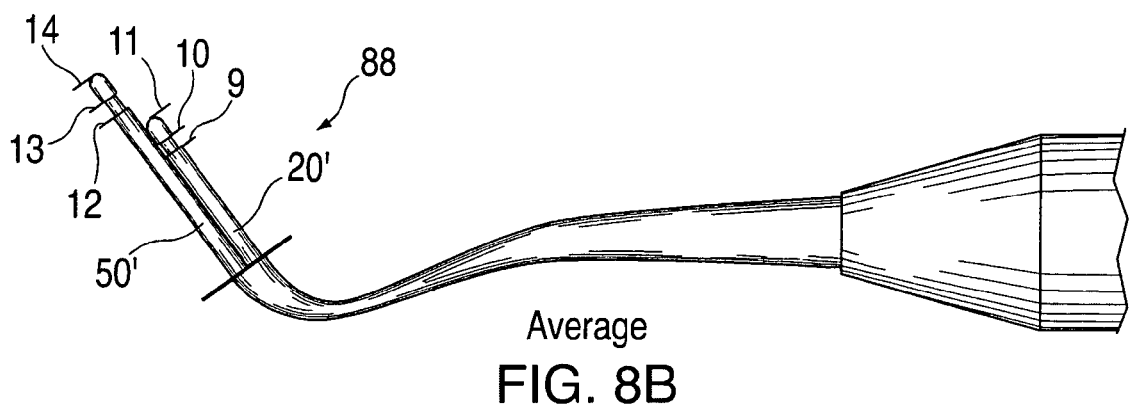
FIG. 8B is a side elevation view of an end of a dental measurement instrument of FIG. 7 for measuring average maxillary teeth.
Figure 8C:
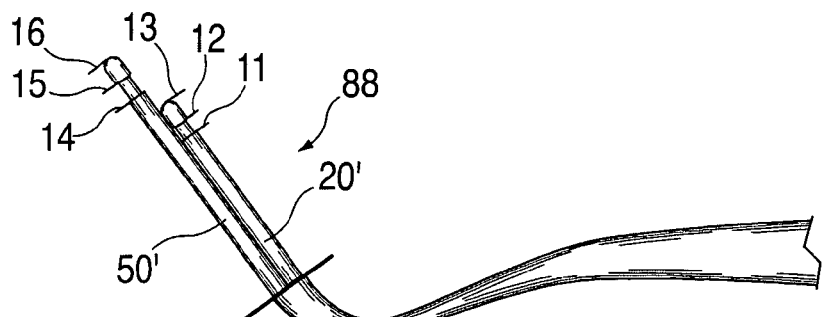
FIG. 8C is a side elevation view of an end of a dental measurement instrument of FIG. 7 for measuring large maxillary teeth.

It has been found that it is preferable to refine the dimensional relationship further by providing small, average and large sizing ranges. A "small" range represents patients having anterior tooth length of 7–9 mm. An "average" range represents patients having anterior tooth length of 9–11 mm. A "large" range represents patients having anterior tooth length of 11–13 mm. Further, by dividing the patient population into these ranges, it is possible to define:

a single numerical value for the length of the clinical crown (and, therefore, the length of the biological crown) of the central incisors;

a single numerical value for the length of the clinical crown (and, therefore, length of the biological crown) of the lateral incisors; and a single numerical value for the length of the clinical crown (and, therefore, length of the biological crown) of the canines;

of the patient being operated on. The relevant distances for maxillary anterior teeth, expressed in millimeters, are illustrated in FIGS. 8A for the small category, 8B for the average category, and 8C for the large category and are set forth in the following Table 3:

TABLE 3

| | MAXILLARY JAW | | | | | |
|---|---|---|---|---|---|---|
| | SIZE | | | | | |
| | SMALL | | AVERAGE | | LARGE | |
| TOOTH | CC | BC | CC | BC | CC | BC |
| Lateral Incisor | 7 | 10 | 9 | 12 | 11 | 14 |
| Canine | 8 | 11 | 10 | 13 | 12 | 15 |
| Central Incisor | 9 | 12 | 11 | 14 | 13 | 16 |

Figure 9A:
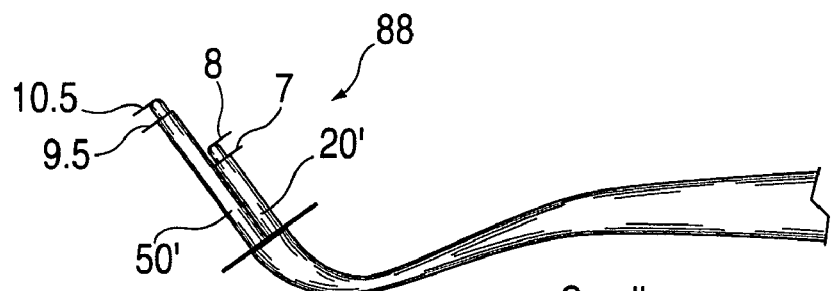
FIG. 9A is a side elevation view of an end of a dental measurement instrument of FIG. 7 for measuring small mandibular teeth.
Figure 9B:
FIG. 9B is a side elevation view of an end of a dental measurement instrument of FIG. 7 for measuring average mandibular teeth.
Figure 9C:
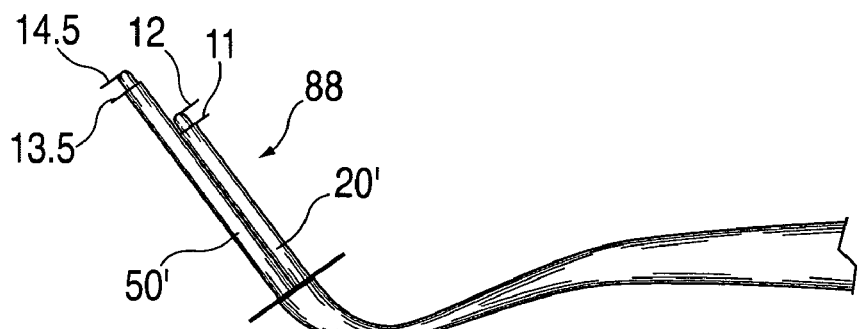
FIG. 9C is a side elevation view of an end of a dental measurement instrument of FIG. 7 for measuring large mandibular teeth.

The relevant distances for mandibular anterior teeth, expressed in millimeters, are illustrated in FIGS. 9A for the small category, 9B for the average category, and 9C for the large category and are set forth in the following Table 4:

TABLE 4

| | MANDIBULAR JAW | | | | | |
|---|---|---|---|---|---|---|
| | SIZE | | | | | |
| | SMALL | | AVERAGE | | LARGE | |
| TOOTH | CC | BC | CC | BC | CC | BC |
| Lateral Incisor | 7 | 9.5 | 9 | 11.5 | 11 | 13.5 |
| Canine | 7 | 9.5 | 9.5 | 12 | 11 | 13.5 |
| Central Incisor | 8 | 10.5 | 10 | 12.5 | 12 | 14.5 |

Because of the morphology and typical dimensions of the mandibular central and lateral incisors of small patients, only a single numerical value for the central and lateral incisors need to be given for the length of the clinical crown (and, therefore, the length of the biological crown) for these patients.

Figure 10:
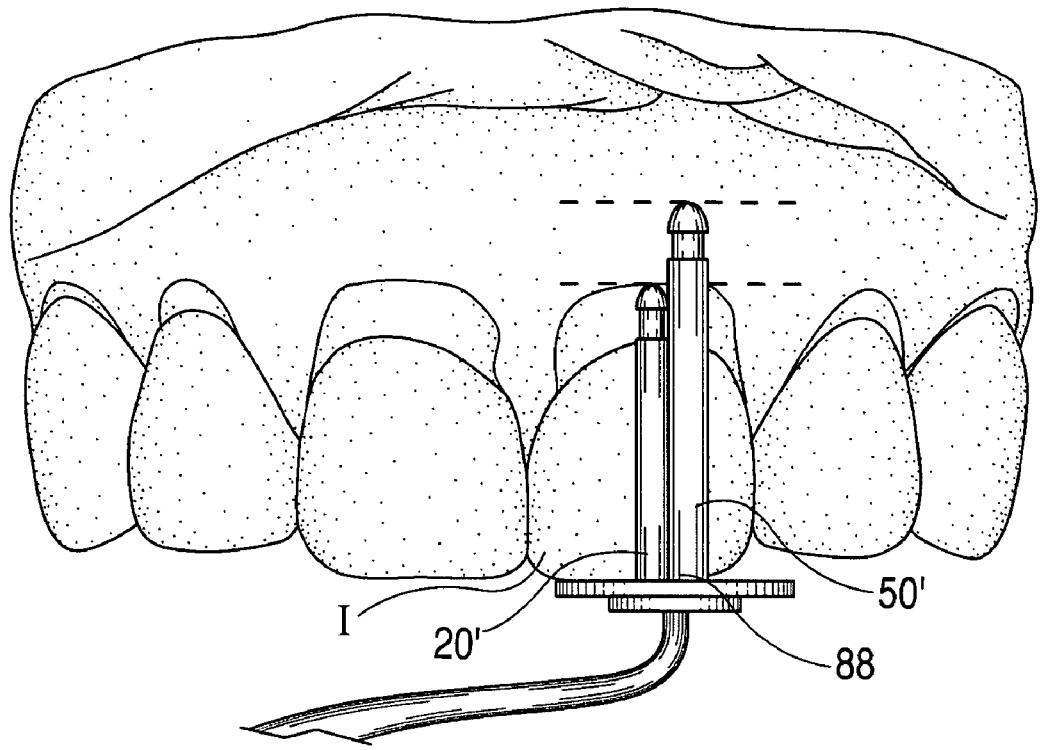
FIG. 10 is a front elevation view of an end of a dental measurement instrument of FIG. 7 illustrating measurement with respect to a left maxillary central incisor.
Figure 11:
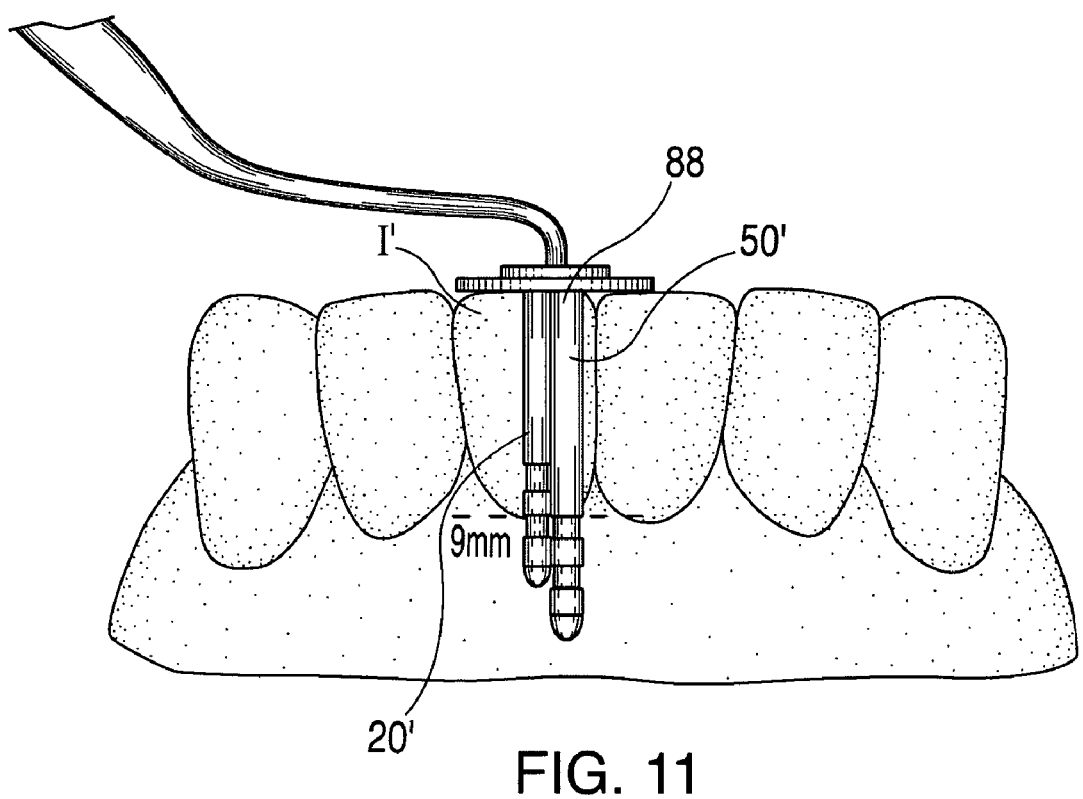
FIG. 11 is a side elevation view of an end of a dental measurement instrument of FIG. 7 illustrating measurement with respect to a right mandibular central incisor.
Figure 12:
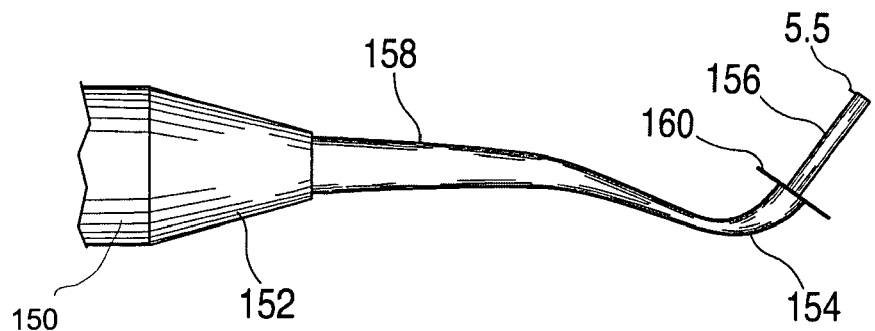
FIG. 12 is a side elevation view, in perspective, of a dental measurement instrument configured in accordance with a third preferred embodiment of the present invention as an interdental papilla position instrument.

FIGS. 10 and 11 illustrate the use of the measuring gauge 88 with respect to a maxillary central incisor I (FIG. 10) and with respect to a mandibular central incisor I' (FIG. 11). As shown in FIG. 10, with the distal end of shaft 20' indicating the clinical crown to be achieved in a lengthening procedure, the corresponding distal end of shaft 50' represents the biologic crown up to the point where a surgeon must remove the tissue.

[Interdental Papilla Position Instrument]

In a third preferred embodiment of the present invention and as shown in FIGS. 12–15, and 16, the dental measurement instrument of the present invention may be in the form of an interdental papilla position instrument 1" for aiding in determining the appropriate position of the interdental papilla of a patient and may comprise a handle 150 with at least one end 152 having an interdental papilla position measuring gauge 154 (FIG. 12) that has a single measuring shaft 156 extending from a support shank 158 and is provided with at least one (see FIG. 15) linear dimension indicia, preferably a plurality (FIG. 13), representing a plurality of fixed distances from the incisal plane for gauging the position of the interdental papilla being evaluated. Preferably, shank 158 may be removably attached to handle 150. The support shank 158 extends from the handle to the measuring gauge 154 and the calibrated measurement shaft 156 in an extended S-shaped curve that serves to align (a) the handle and (b) the calibrated measurement shaft 156 with respect to each other so that the calibrated measurement shaft 156 can be placed against a tooth with the handle being in a comfortable orientation for the user.

The interdental papilla is the portion of gingival tissue that is disposed between two adjacent teeth and that extends into the space between two adjacent teeth. The height of the interdental papilla is desirably 50% of the length of the tooth.

Figure 13A:
FIG. 13A is a side elevation view of a dental measurement instrument of FIG. 12 for small maxillary teeth.
Figure 13B:
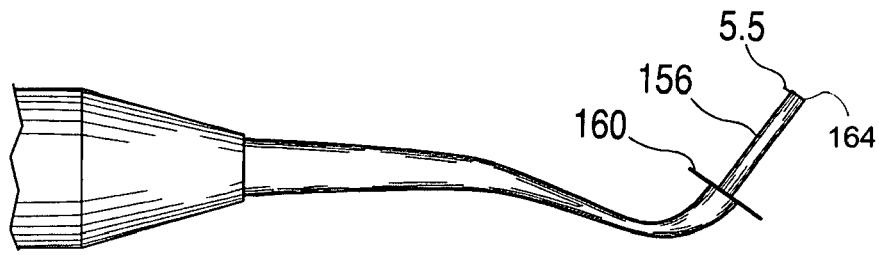
FIG. 13B is a side elevation view of a dental measurement instrument of FIG. 12 for average maxillary teeth.
Figure 13C:
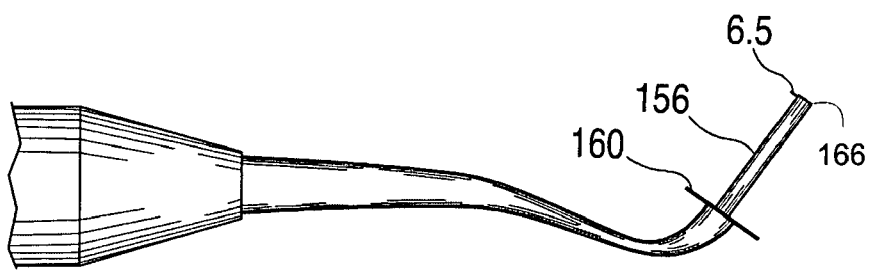
FIG. 13C is a side elevation view of a dental measurement instrument of FIG. 12 for large maxillary teeth.

The measuring gauge 154 may be provided with a transverse stop collar 160 at the intersection of the measurement shaft 156 with the support shank 158 to facilitate measurement, the collar 160 acting as an abutment against the tooth under consideration or analysis. It has been found that it is preferable to refine the dimensional relationships further by providing small, average and large sizes. (A "small" range represents patients having anterior tooth length of 7–9 mm. An "average" range represents patients having anterior tooth length of 9–11 mm. A "large" range represents patients having anterior tooth length of 11–13 mm.). The relevant interdental papillar distances for maxillary anterior teeth, expressed in millimeters, is illustrated in FIG. 13 at 162 for the small category, 164 for the average category, and 166 for the large category and are set forth in the following Table 5:

TABLE 5

MAXILLARY JAW

| | SIZE | | |
|---|---|---|---|
| | SMALL LENGTH | AVERAGE LENGTH | LARGE LENGTH |
| Papilla | 4.5 | 5.5 | 6.5 |

Figure 14A:
FIG. 14A is a side elevation view of a dental measurement instrument of FIG. 12 for small mandibular teeth.
Figure 14B:
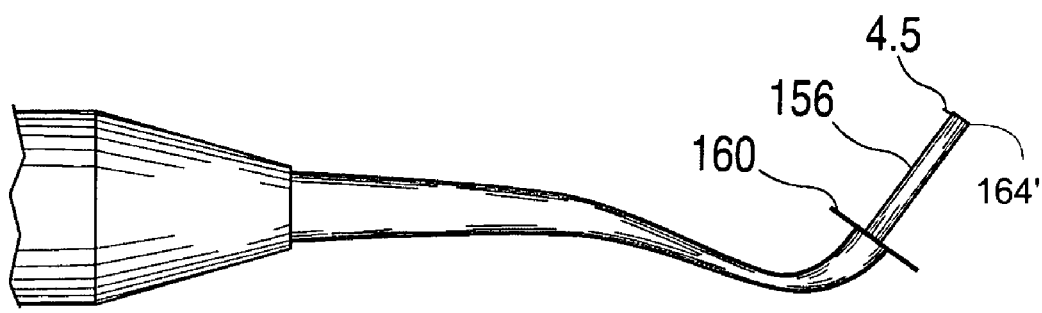
FIG. 14B is a side elevation view of a dental measurement instrument of FIG. 12 for average mandibular teeth.
Figure 14C:
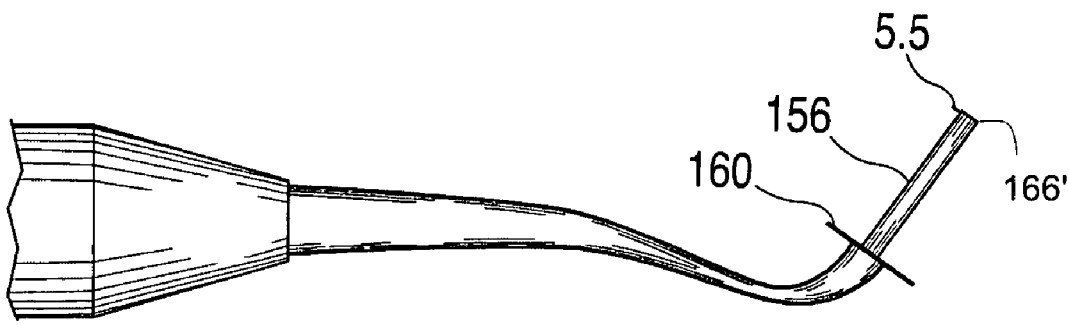
FIG. 14C is a side elevation view of a dental measurement instrument of FIG. 12 for large mandibular teeth.

The relevant interdental papillar distances for mandibular anterior teeth, expressed in millimeters, is illustrated in FIG. 14 at 162' for the small category, 164' for the average category, and 166' for the large category and are set forth in the following Table 6:

TABLE 6

MANDIBULAR JAW

| | SIZE | | |
|---|---|---|---|
| | SMALL LENGTH | AVERAGE LENGTH | LARGE LENGTH |
| Papilla | 3.5 | 4.5 | 5.5 |

Figure 15:
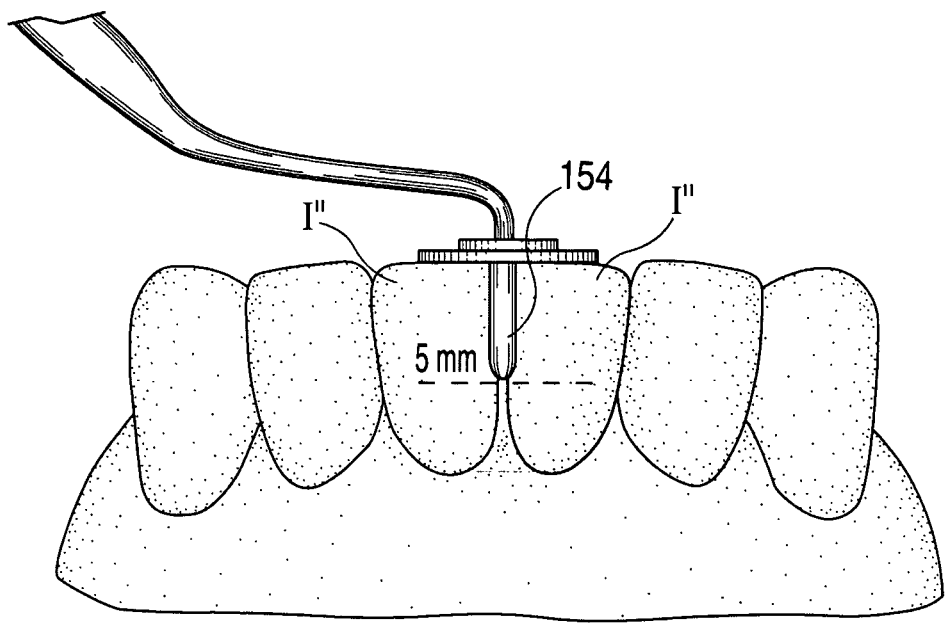
FIG. 15 is a side elevation view of a dental measurement instrument of FIG. 12 illustrating measurement with respect to the interdental papilla of right and left mandibular central incisors.
Figure 16:
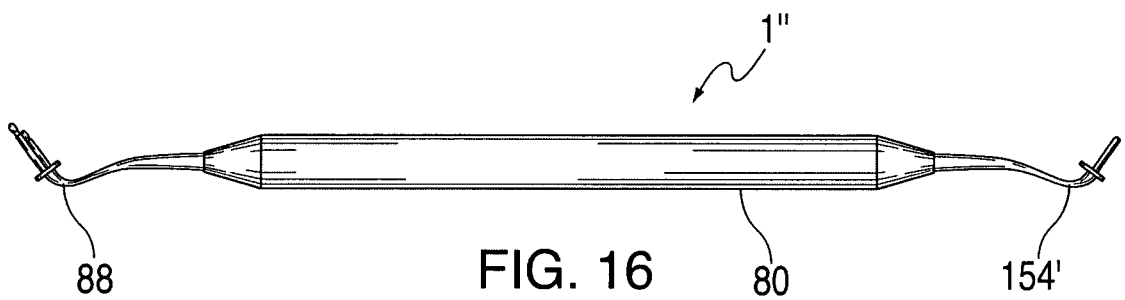
FIG. 16 is a side elevation view, in perspective, of a dental measurement instrument configured in accordance with both the second and the third preferred embodiments of the present invention as a periodontal surgical gauge instrument and an interdental papilla position instrument.
Figure 17:
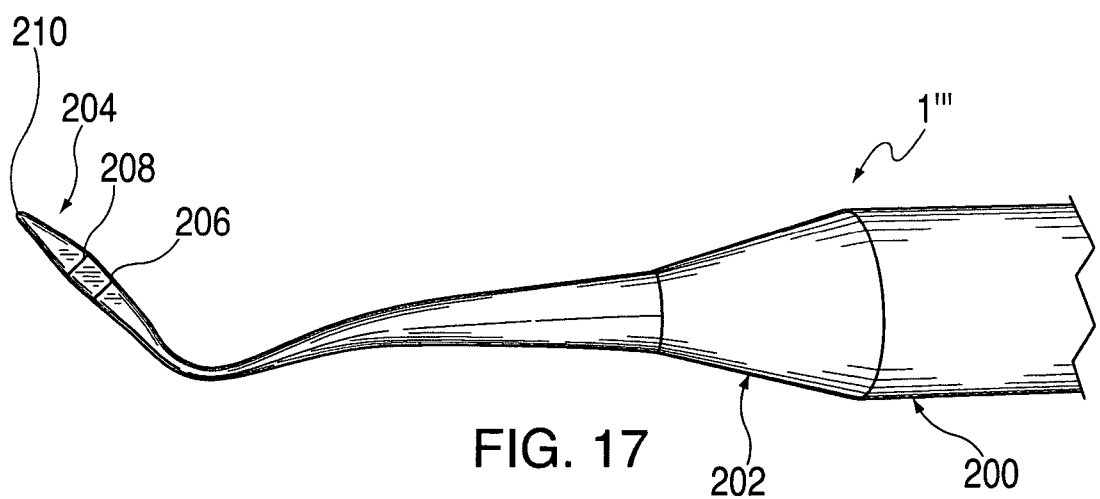
FIG. 17 is a side elevation view of a dental measurement instrument configured in accordance with a fourth preferred embodiment of the present invention as a periodontal bone sounding instrument.
Figure 21:
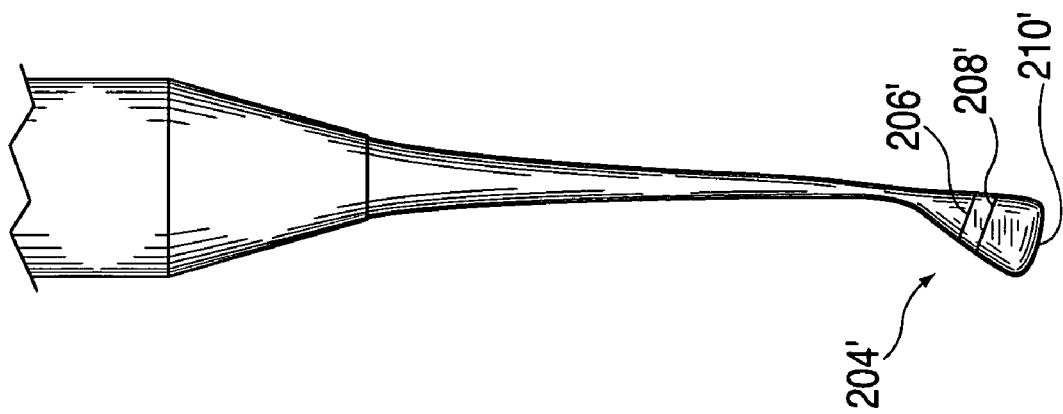
FIG. 21 is a top plan view of a dental measurement instrument of FIG. 20.
Figure 20:
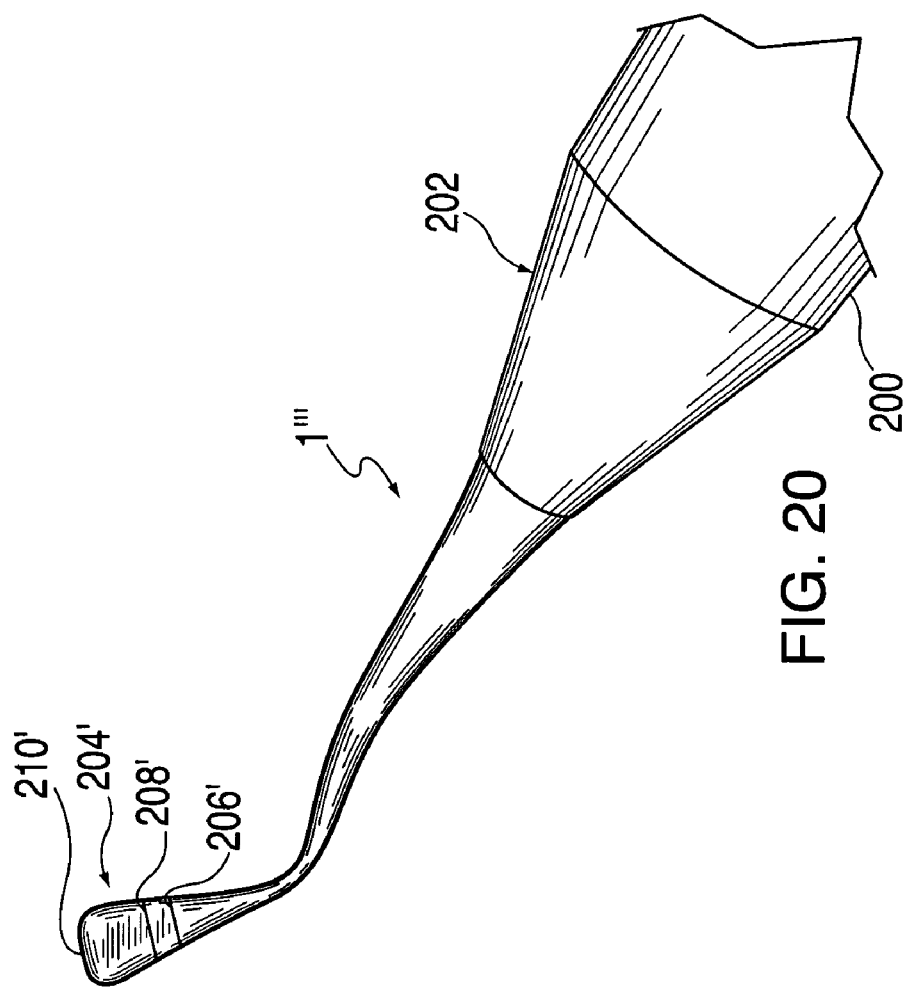
FIG. 20 is a side elevation view, in perspective, of a second form of a dental measurement instrument configured in accordance with a fourth preferred embodiment of the present invention as a periodontal bone sounding instrument.
Figure 22:
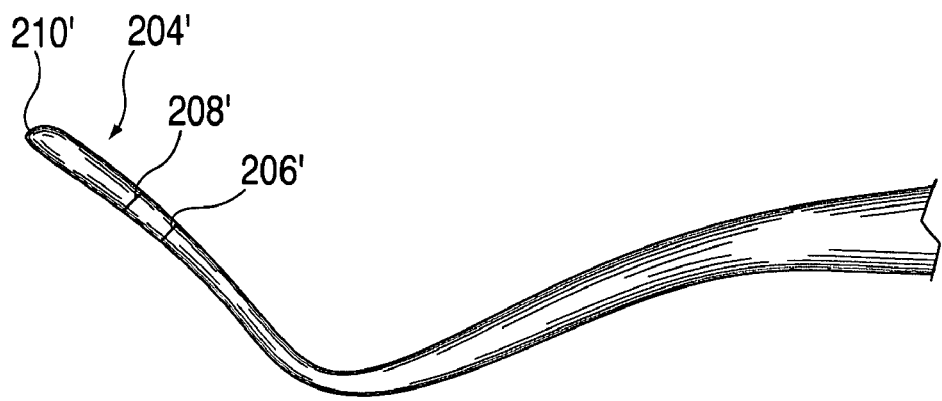
FIG. 22 is an enlarged side elevation view, in perspective, of a dental measurement instrument of FIG. 20.
Figure 23:
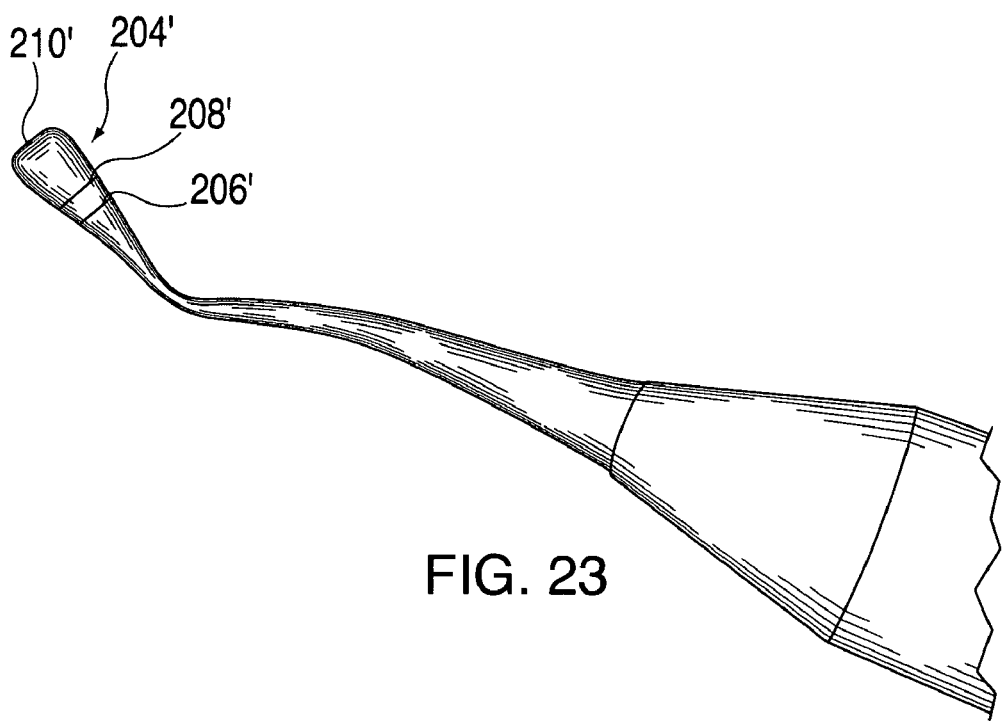
FIG. 23 is an enlarged side elevation view, in perspective, of a dental measurement instrument of FIG. 20.
Figure 24:
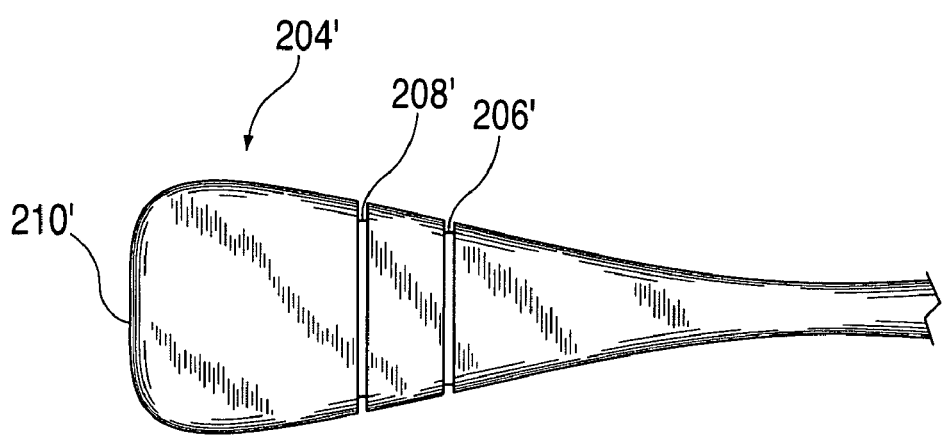
FIG. 24 is an enlarged top plan view of a dental measurement instrument of FIG. 20.
Figure 25:
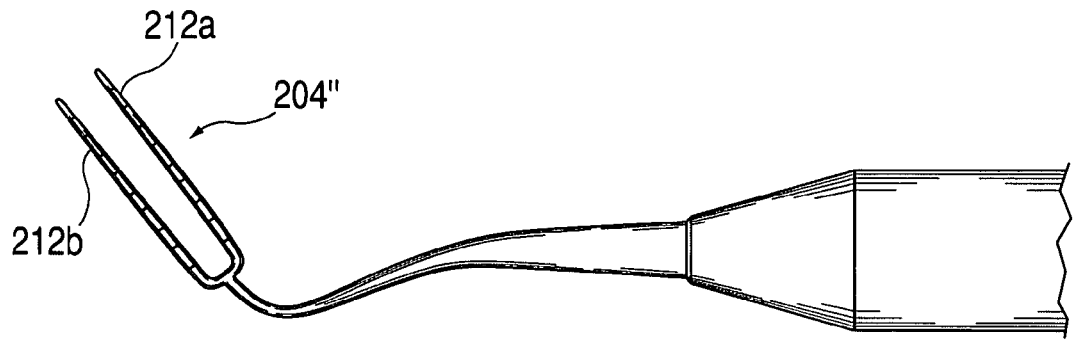
FIG. 25 is a side elevation view of a third form of a dental measurement instrument configured in accordance with a fourth preferred embodiment of the present invention as a periodontal bone sounding instrument.
Figure 26:
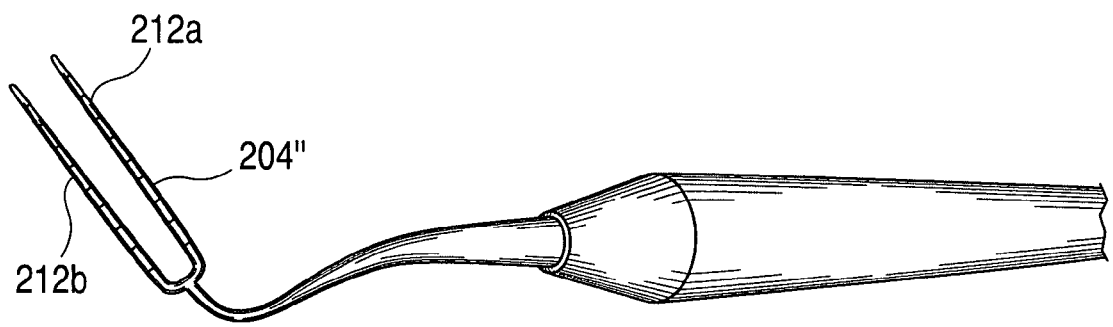
FIG. 26 is a front elevation view, in perspective, of a dental measurement instrument of FIG. 25.
Figure 27:
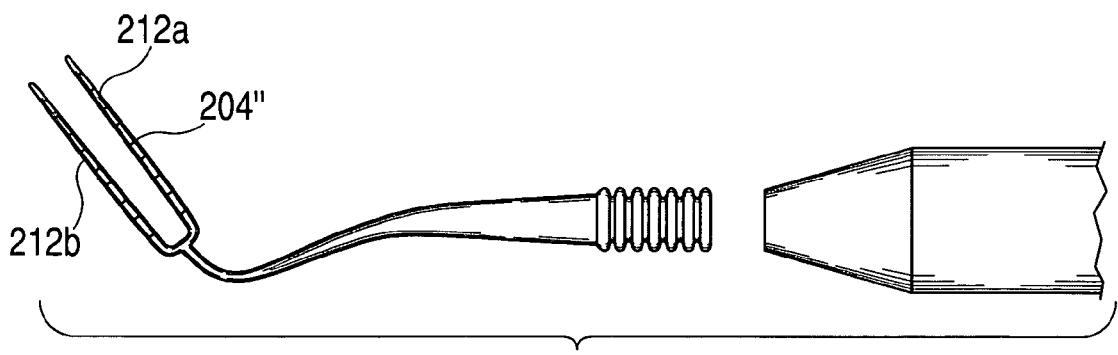
FIG. 27 is a side front elevation view, in perspective, of a dental measurement instrument of FIG. 25 illustrating detachment.

FIG. 15 illustrates the use of the interdental papilla position measuring gauge 154 with respect to measuring the position of the interdental papilla between the mandibular central incisors I''.

In an alternative embodiment of both the periodontal surgical gauge instrument 1' and the interdental papilla position instrument 1'' of the present invention, a periodontal surgical gauge instrument 1' may be provided with an interdental papilla position measuring gauge 154' on the end of the handle 80 distal to the end from which the crown measuring gauge extends. (See FIG. 16.). In this way the length of the clinical and biological crowns can be conveniently measured in concert with the interdental papilla position.

[Periodontal Bone Sounding Instrument]

In a fourth preferred embodiment of the present invention and as shown in FIGS. 17–27, the dental measurement instrument of the present invention may be in the form of a periodontal bone sounding instrument 1''' for aiding in determining the location of the bone of the osseous crest of the maxilla (or the mandible) and may comprise a handle 200 with two opposed ends and at least one end 202 having a bone sounding probe 204 extending from it. Preferably the sounding probe 204 is removably attached to handle 200. It is desirable to determine the location of the gingival margin with respect to the osseous crest in order to know whether it is necessary to resect or to provide a flap. If the instrument indicates a distance of more than 3 mm from the osseous crest to the gingival margin, then it is not necessary to remove bone. If the instrument indicates a distance of less than 3 mm from the osseous crest to the gingival margin, then removal of bone is necessary.

In a first form, the bone sounding probe 204 is curved in side elevation (FIGS. 17–19) and provided with a plurality of linear distance indicia 206 and 208. The blade has a curvature of about 4° in order to conform generally to the curvature of a tooth. In this way, the blade can be slid into and through the space between the tooth and the gingiva until the tip makes contact with the bone. The probe 204 is a leaf-shaped blade that is broader at its center portion and arcuately tapered toward its distal and its proximal ends with the proximal end merging into a round attachment shaft. The probe 204 is provided with a rounded, blunt tip 210 configured to make blunt (nonpenetrating) contact with bone without penetrating it so that an accurate measurement is taken with the bone being the reference origin for the measurement rather than the tip being embedded some indefinite distance into the bone. The blade is relatively thin to allow insertion between the tooth and the gingival. As may be seen from the top view in FIG. 18, the attachment of the blade with respect to the handle may be curvedly offset at an angle to the right to permit right-handed use of the instrument. Similarly the offset may be to the left for left-handed use.

The indicia preferably indicate a depth of 3.0 mm from the tip for indicia 208 and a depth of 4.5 mm. from the tip for indicia 206. The indicia may be color-coded for clarity.

In a second form of the bone sounding probe 204' (FIGS. 20–24), the probe 204' is spatulate in form (see FIG. 24 in particular) so that the distal end or tip 210' is the widest portion of the probe and the probe expands in width from the proximal end to the distal end. The increased width distal end makes contact with the bone of the osseous crest along a linear or rectangular probe contact surface. Desirably, the probe is curved as in the first form of the probe 204. The indicia 206' and 208' may be provided by color-coding or by relief grooves. (See FIG. 24.).

In a third form of the bone sounding probe 204'' (FIGS. 25–27) the probe is bifurcated with two tapered distal shafts 212a and 212b available to make contact with the bone of the osseous crest, thereby affording two alternative end points for making contact. Each shaft 212a and 212b may be provided with a plurality of indicia as aforesaid for measuring distance as aforesaid.

In using the periodontal bone sounding instrument for determining the location of the gingival margin of a tooth with respect to the osseous crest of a tooth as a reference point, the dimensionally calibrated measuring gauge of the instrument is placed with its origin (tip 210, tip 210' or tip 210'') abutting the osseous crest of a tooth as a reference point and the position of the gingival margin of the tooth with respect to measuring gauge is read from the indicia 206, 208 etc.

I claim:

1. A dental measurement instrument comprising: a handle having opposite ends; and a measuring gauge extending from at least one end of said handle, comprising: a first measurement shaft bearing a first set of calibration indicia; and a second measurement shaft bearing a second set of calibration indicia; wherein indicia of said first set of calibration indicia correspond to indicia of said second set of calibration indicia in a specific predetermined mathematical relationship.

2. The dental measurement instrument as recited in claim 1 wherein said first and second sets of calibration indicia are represented by corresponding markings.

3. The dental measurement instrument as recited in claim 2 wherein said corresponding markings are corresponding spaced apart grooves.

4. The dental measurement instrument as recited in claim 2 wherein said corresponding markings are corresponding colors.

5. The dental measurement instrument as recited in claim 1 wherein said first set of calibration indicia indicates a first distance measurement on said first measurement shaft and said second set of calibration indicia indicates a corresponding second distance measurement that is the outcome of said predetermined mathematical relationship.

6. The dental measurement instrument as recited in claim 5 wherein said first distance measurement is for tooth width and said second distance measurement is for tooth length.

7. The dental measurement instrument as recited in claim 5 wherein said first distance measurement is for tooth length and said second distance measurement is for tooth width.

8. The dental measurement instrument as recited in claim 5 wherein said first distance measurement is for the length of the position of the clinical crown of a tooth and said second measurement distance is for the length of the position of the biologic crown of the tooth.

9. The dental measurement instrument as recited in claim 1, wherein said measuring gauge is removably attached to said handle.

10. The dental measurement instrument as recited in claim 1, wherein said second measurement shaft is in pivotable relationship with said first measurement shaft.

11. The tooth proportion instrument in accordance with claim 1, wherein said first measurement shaft is disposed transversely of said second measurement shaft.

12. The tooth proportion instrument in accordance with claim 1, wherein said first measurement shaft is disposed perpendicularly of said second measurement shaft.

13. The tooth proportion instrument in accordance with claim 1, wherein said first measurement shaft is disposed at a right angle to said second measurement shaft to form an inverted T-shaped configuration.

* * * * *